(12) United States Patent
Koga et al.

(10) Patent No.: US 11,832,921 B2
(45) Date of Patent: Dec. 5, 2023

(54) BLOOD PRESSURE METER

(71) Applicant: OMRON HEALTHCARE CO., LTD., Muko (JP)

(72) Inventors: Toshiaki Koga, Kyoto (JP); Takuya Nagata, Kyoto (JP); Toshihiko Ogura, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 605 days.

(21) Appl. No.: 17/061,390

(22) Filed: Oct. 1, 2020

(65) Prior Publication Data

US 2021/0030287 A1    Feb. 4, 2021

Related U.S. Application Data

(63) Continuation of application No. PCT/JP2019/007788, filed on Feb. 28, 2019.

(30) Foreign Application Priority Data

Apr. 10, 2018  (JP) .................................. 2018-075591

(51) Int. Cl.
*A61B 5/022*  (2006.01)
*A61B 5/00*  (2006.01)

(52) U.S. Cl.
CPC ........ *A61B 5/02233* (2013.01); *A61B 5/7405* (2013.01)

(58) Field of Classification Search
CPC ... A61B 5/02233; A61B 5/7405; A61B 5/022; A61B 5/742; A61B 5/02141; A61B 2560/04; A61B 2560/0406; A61B 2562/16
See application file for complete search history.

(56) References Cited

U.S. PATENT DOCUMENTS

| 5,735,798 A | * | 4/1998 | Shinohara | .......... A61B 5/02241 |
| | | | | 600/490 |
| 2004/0079550 A1 | * | 4/2004 | Lange | ...................... E02D 1/04 |
| | | | | 175/58 |
| 2006/0184053 A1 | | 8/2006 | Yang | |

FOREIGN PATENT DOCUMENTS

JP    S62-87610 U    6/1987
JP    H02-17031 A    1/1990
(Continued)

OTHER PUBLICATIONS

English-language machine translation of JP-2005028123-A (Year: 2023).*

(Continued)

*Primary Examiner* — Andrey Shostak
(74) *Attorney, Agent, or Firm* — Oliff PLC

(57) ABSTRACT

In a sphygmomanometer of the present invention, a main body includes a slide receiving part having a circular-arc cross section that opens upward and slidably receiving a cuff unit along a direction perpendicular to the circular-arc cross-section. The cuff unit includes a cylindrical cuff structure having a fluid bag along the inner circumferential surface, and a cover having a circular-arc cross section that opens downward and detachably attached integrally with the cuff structure to cover the upper half of the cuff structure. When the cuff unit is slid along the slide receiving part, upper edges on both sides of the circular-arc cross section of the slide receiving part abut with the lower edges on both sides of the circular-arc cross section of the cover to support the weight of the cuff unit.

9 Claims, 16 Drawing Sheets

(56) References Cited

FOREIGN PATENT DOCUMENTS

| | | | | |
|---|---|---|---|---|
| JP | H0217031 | A | * | 1/1990 |
| JP | 2005-028123 | A | | 2/2005 |
| JP | 2005028123 | A | * | 2/2005 |
| JP | 2005-237802 | A | | 9/2005 |
| JP | 2005-245952 | A | | 9/2005 |
| JP | 2005245952 | A | * | 9/2005 |
| JP | 2005-334048 | A | | 12/2005 |
| JP | 2006-204543 | A | | 8/2006 |
| WO | 2005/074793 | A1 | | 8/2005 |

OTHER PUBLICATIONS

English-language machine translation of JP-2005245952-A (Year: 2023).*

English-language machine translation of portions of JP-H0217031-A (Year: 2023).*

May 28, 2019 International Search Report issued in International Patent Application No. PCT/JP2019/007788.

* cited by examiner

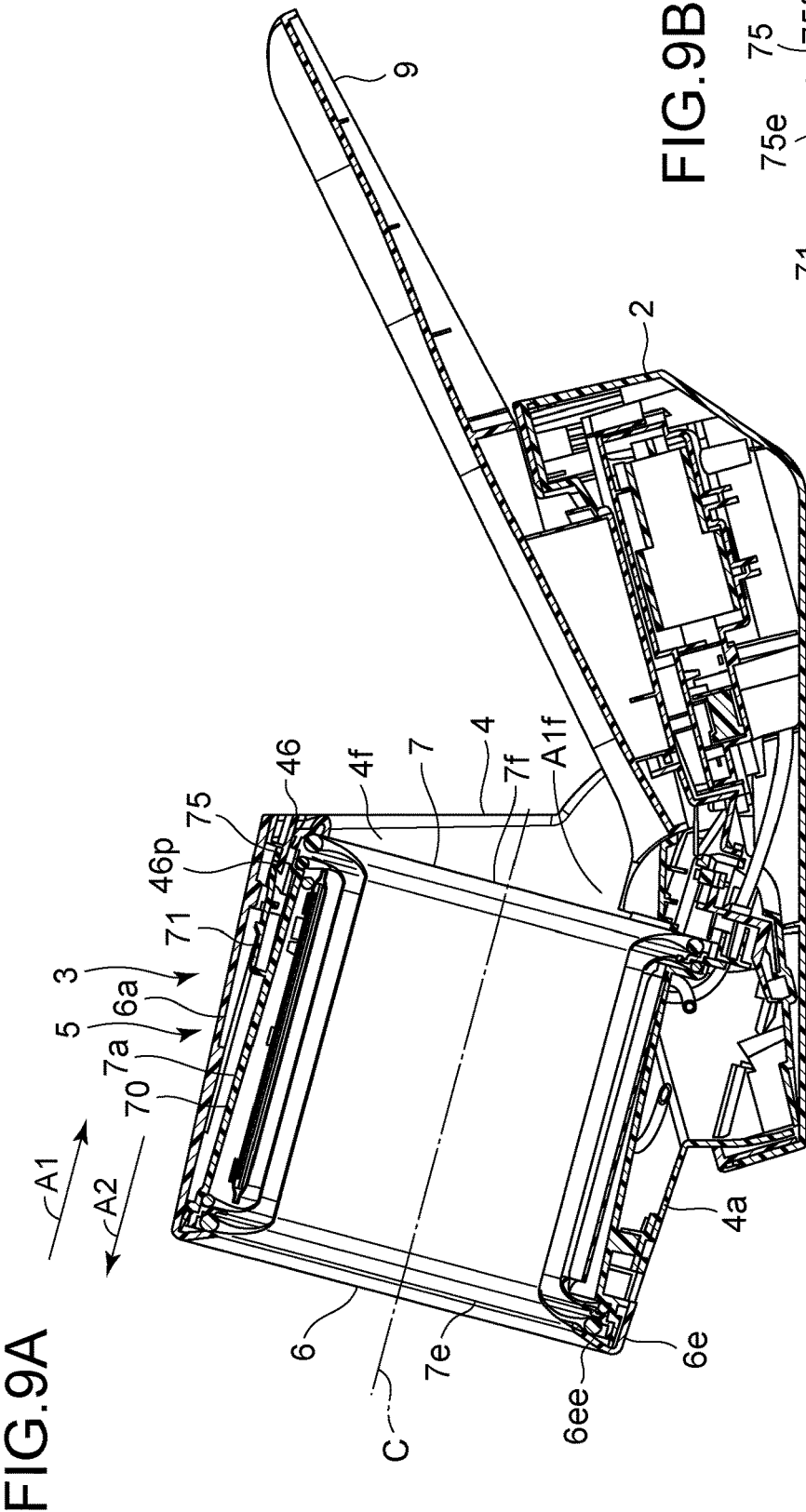
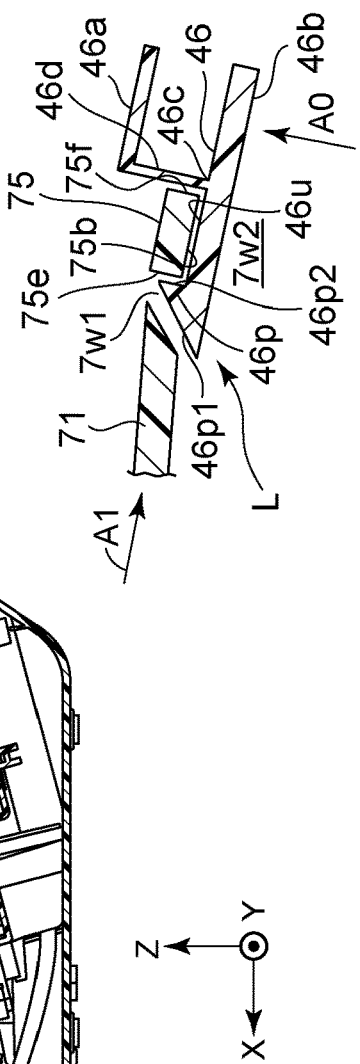
FIG.9A
FIG.9B

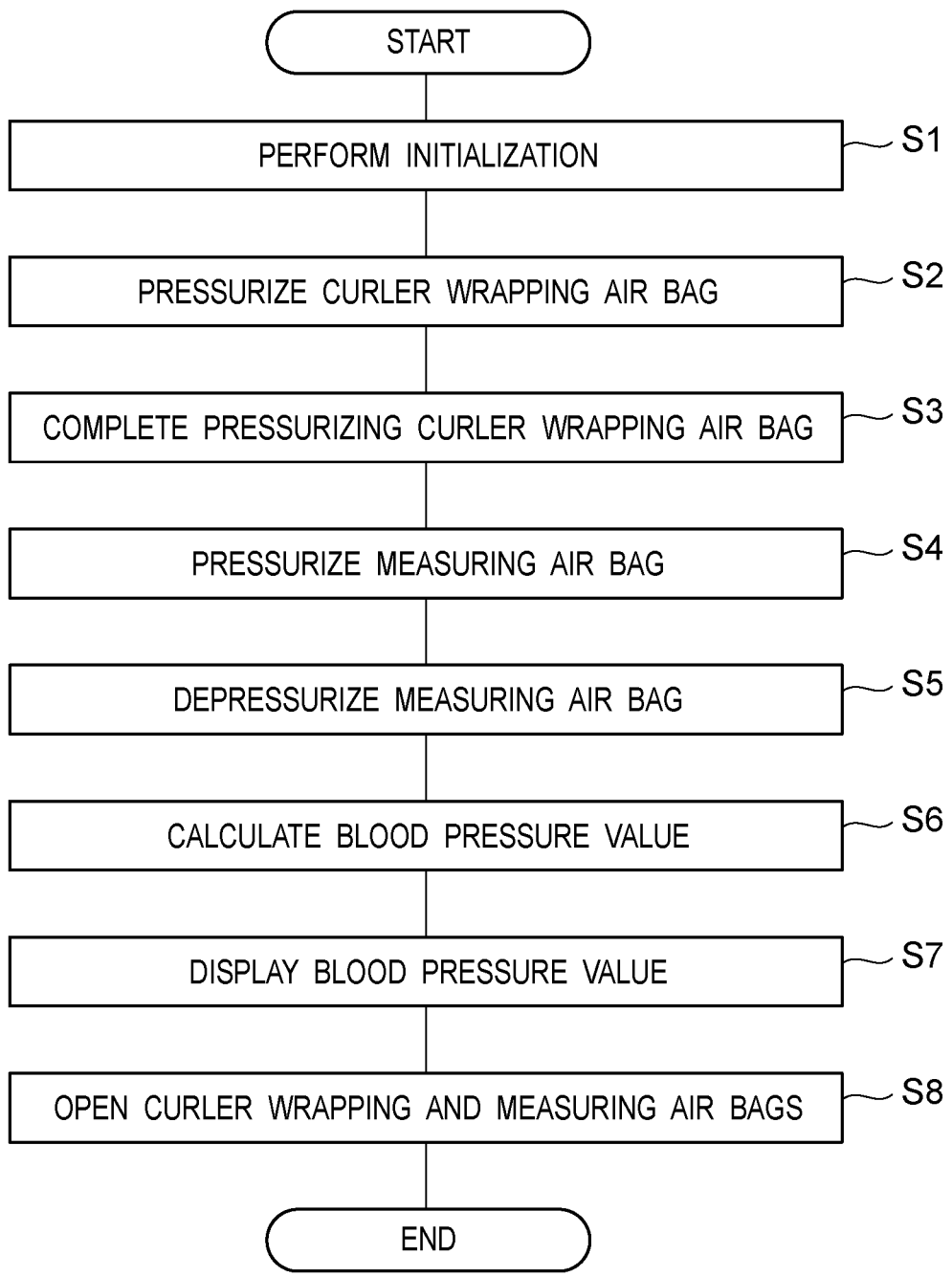

BLOOD PRESSURE METER

CROSS-REFERENCE TO RELATED APPLICATION

This is a continuation application of International Application No. PCT/JP2019/007788, with an International filing date of Feb. 28, 2019, which claims priority of Japanese Patent Application No. 2018-075591 filed on Apr. 10, 2018, the entire content of which is hereby incorporated by reference.

TECHNICAL FIELD

The present invention relates to a sphygmomanometer, and more particularly, to a sphygmomanometer including a main body accommodating a pump and a cylindrical cuff unit detachably attached to the main body.

BACKGROUND ART

Conventionally, as this type of sphygmomanometer, for example, there is known one disclosed in Patent Literature 1 (JP 2005-334048 A) including a main body accommodating a pump and a cylindrical cuff unit detachably attached to the main body. A cuff part constituted of a cloth bag or a rubber bag is provided in the inner circumferential surface of the cuff unit. During blood pressure measurement, with the upper arm of a subject inserted into the cuff, air is supplied from the pump of the main body to the cuff part of the cuff unit to compress the upper arm. Thereby, the blood pressure measurement is performed.

SUMMARY OF INVENTION

Incidentally, when the above-described sphygmomanometer is used for many years, for example, a fluid bag (a cuff part constituted of a cloth or rubber bag, also referred to as an air bag) may deteriorate, and defects such as air leakage may occur. In that case, as the conventional general measure, only the cuff unit is replaced with a new one from the viewpoint of cost saving.

Here, as a result of many years of use, the main body usually has discolored. For this reason, when a new cuff unit is attached to the above main body, the difference in color between the discolored main body and the new cuff unit may give the user an odd feeling.

Therefore, it is an object of the present invention to provide a sphygmomanometer including a main body accommodating a pump and a cylindrical cuff unit detachably attached to the main body, in which a component is exchanged easily, and the user is prevented from feeling odd even if the component is exchanged.

In order to solve the above-mentioned problem, a sphygmomanometer of the present disclosure comprises:
a main body accommodating a pump; and
a cuff unit having a cylindrical shape and detachably attached to the main body,
wherein the main body includes a slide receiving part having a circular-arc cross section that opens upward and slidably receiving the cuff unit along a direction perpendicular to the circular-arc cross section,
wherein the slide receiving part is tilted horizontally or in a manner of gradually increasing in height toward a slide end side in a sliding direction of sliding the cuff unit,
wherein the cuff unit includes
a cuff structure having a cylindrical shape so as to allow a measurement target site having a rod shape to be inserted, and having a fluid bag along an inner circumferential surface, and
a cover having a circular-arc cross section that opens downward, and detachably attached integrally to the cuff structure to cover at least an upper half of the cuff structure, and
wherein, when the cuff unit is slid along the slide receiving part, upper edges of both sides of the circular-arc cross section of the slide receiving part come into contact with lower edges of both sides of the circular-arc cross section of the cover to support a weight of the cuff unit.

Here, with respect to the cuff unit, "down" in the "downward" and "upper" in the "upper half" refer to the sides that become "lower" and "upper" sides, respectively, in a state of the cuff unit being attached to the main body.

BRIEF DESCRIPTION OF DRAWINGS

The present invention will become more fully understood from the detailed description given hereinbelow and the accompanying drawings which are given by way of illustration only, and thus are not limitative of the present invention, and wherein:

FIG. 9A is a diagram showing a cross section of the sphygmomanometer as viewed from the right side. FIG. 9B is an enlarged diagram of a lock part of FIG. 9A that engages the main body with the cuff unit.

FIG. 16 is a diagram showing an operation flow of blood pressure measurement in the sphygmomanometer.

DESCRIPTION OF EMBODIMENTS

Hereinafter, an embodiment of the present invention is described in detail with reference to the drawings.
(Schematic Configuration of Main Body)

Figure 1:
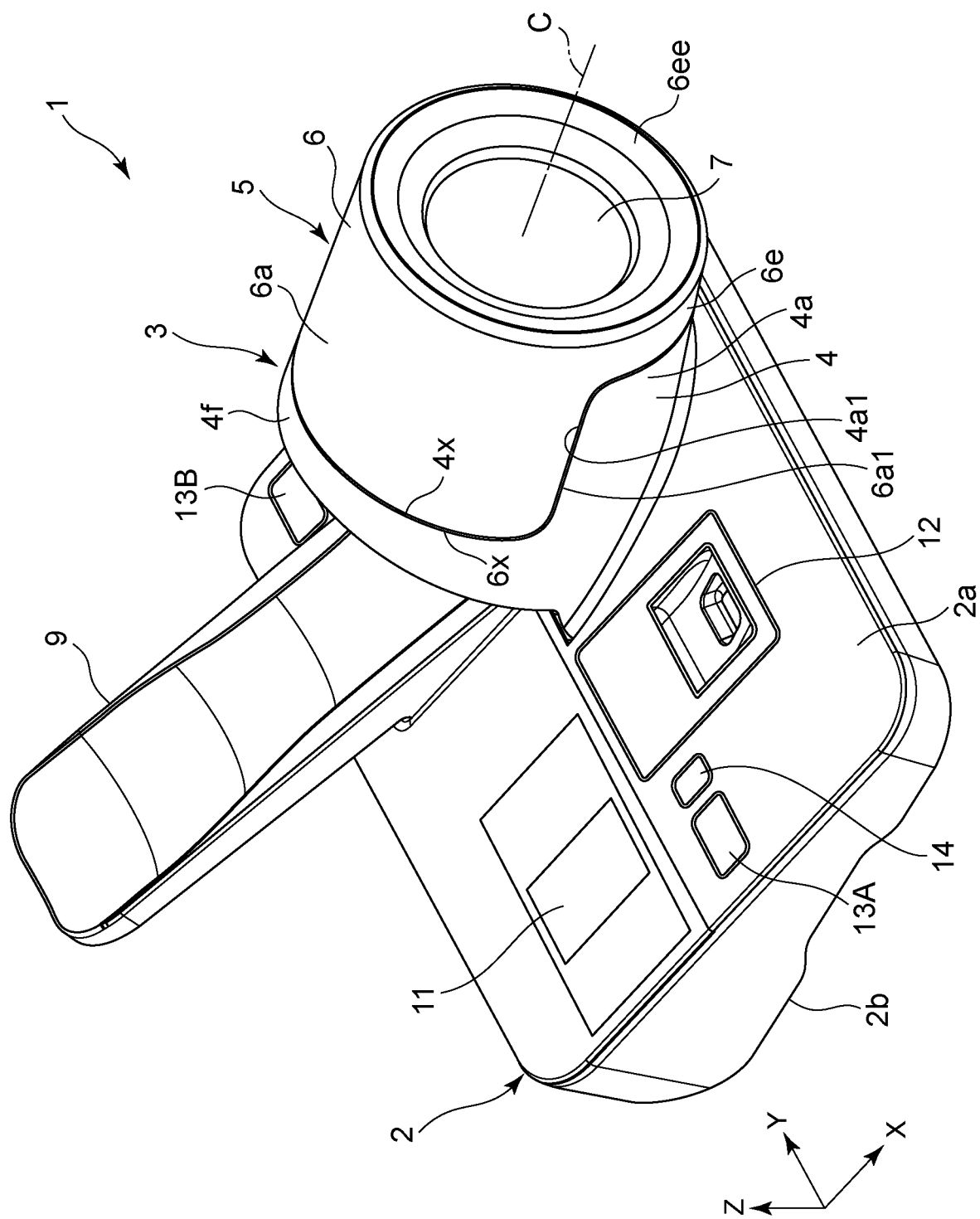
FIG. 1 is a diagram showing a sphygmomanometer according to one embodiment of the present invention as viewed diagonally from above and front.
Figure 2:
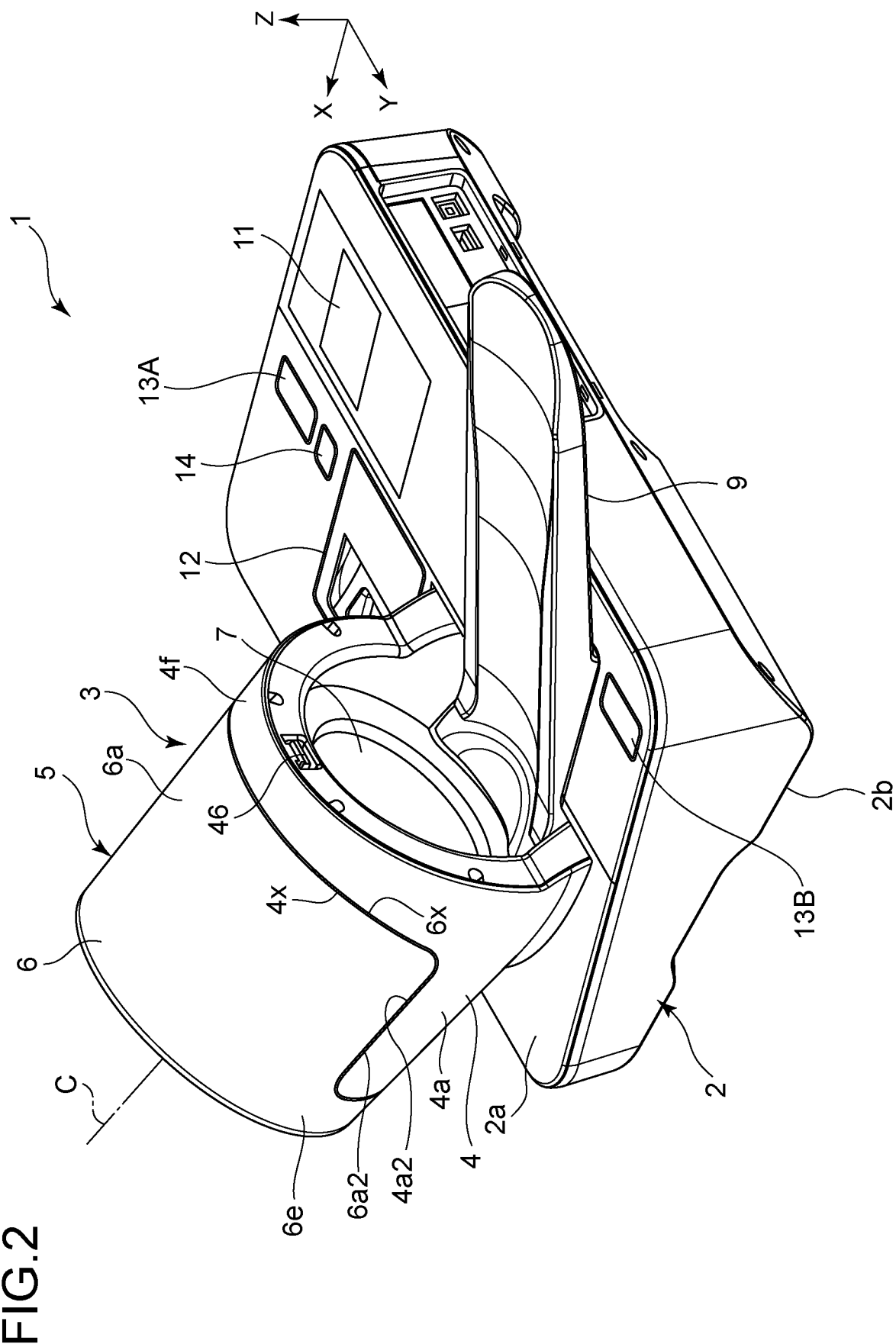
FIG. 2 is a diagram showing the sphygmomanometer as viewed diagonally from above and rear.
Figure 3:
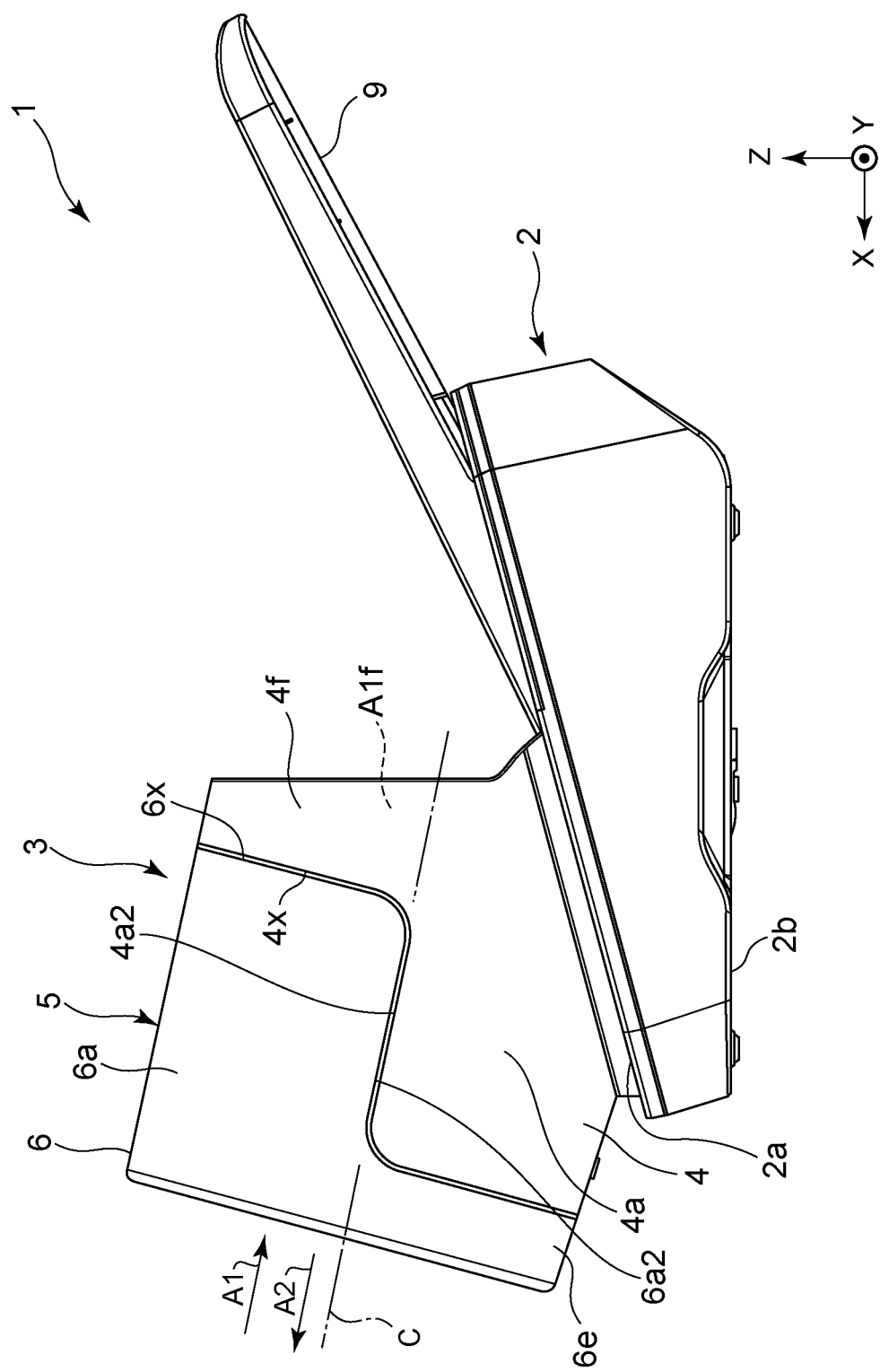
FIG. 3 is a diagram showing the sphygmomanometer as viewed from the right side.

FIG. 1 shows a sphygmomanometer (indicated by reference numeral 1) of one embodiment of the present invention as viewed from diagonally above and front. FIG. 2 shows the sphygmomanometer 1 as viewed diagonally from above and rear. Further, FIG. 3 shows the sphygmomanometer 1 as viewed from the right side. Note that these FIGS. 1 to 3 (and FIGS. 4, 9, and 11 described later) also show an XYZ orthogonal coordinate system for easy understanding. The X-axis is oriented in the front-back direction, the Y-axis is oriented in the left-right direction, and the Z-axis is oriented in the up-down direction. As shown in FIGS. 1 to 3, the sphygmomanometer 1 generally includes a main body 2, a cuff 3, and an armrest 9. The sphygmomanometer 1 is designed to measure the blood pressure of the upper arm of a subject as a measurement target site.

The main body 2 has a box-like outer shape with rounded corners. A bottom surface 2b of the main body 2 is substantially flat, and is placed on a not-shown horizontal plane (a table-like surface along the XY plane). An upper surface 2a of the main body 2 is substantially flat and is tilted in a manner of gradually increasing in height (increasing in Z coordinate) from the front to the rear (in the −X direction).

A substantially cylindrical cuff 3 is arranged on the right front part of the upper surface 2a of the main body 2. In this example, the central axis C of the cuff 3 (that is, the central axis of the slide receiving part 4 to be described later) is tilted in a manner of gradually decreasing in height (decreasing in Z coordinate) from the front to the rear (in the −X direction).

An armrest 9 is arranged on the right rear part of the upper surface 2a of the main body 2. The armrest 9 has a substantially circular-arc cross section that opens upward, and extends substantially straight and rearward of the main body 2 from an opening on the rear surface side of the cuff 3 at a steeper tilt than the tilt of the upper surface 2a of the main body 2. During blood pressure measurement, the subject sits in front of the main body 2 and passes the arm from the front surface side (the side facing the subject) to the rear surface side of the cuff 3 such that the upper arm of the subject is expected to be placed inside the cuff 3 and the forearm is expected to be placed on the armrest 9.

Among the upper surface 2a of the main body 2, there are provided on the left front part, a measurement start/stop switch 13A for allowing a user (mainly a subject. The same applies hereinafter) to instruct the start or stop of measurement with the left hand, and a print instruction switch 14 for allowing the user to instruct printing of the blood pressure measurement result. Among the upper surface 2a of the main body 2, there is arranged on the left rear part, a display (a liquid crystal display (LCD) in this example) 11 for displaying the blood pressure measurement result. The display 11 may be erected on the upper surface 2a of the main body 2 such that a display screen faces the subject. Further, on the upper surface 2a of the main body 2, there is arranged on the further right side of the armrest 9, a measurement start/stop switch 13B for allowing the user to instruct the start or stop of the measurement with the right hand. The two measurement start/stop switches 13A and 13B are provided for convenience when the subject passes the right upper arm or left upper arm through the cuff 3 for measurement.

The cuff 3 is constituted of a slide receiving part 4 provided in the main body 2 and a cylindrical cuff unit 5 detachably attached to the slide receiving part 4.

Figure 4:
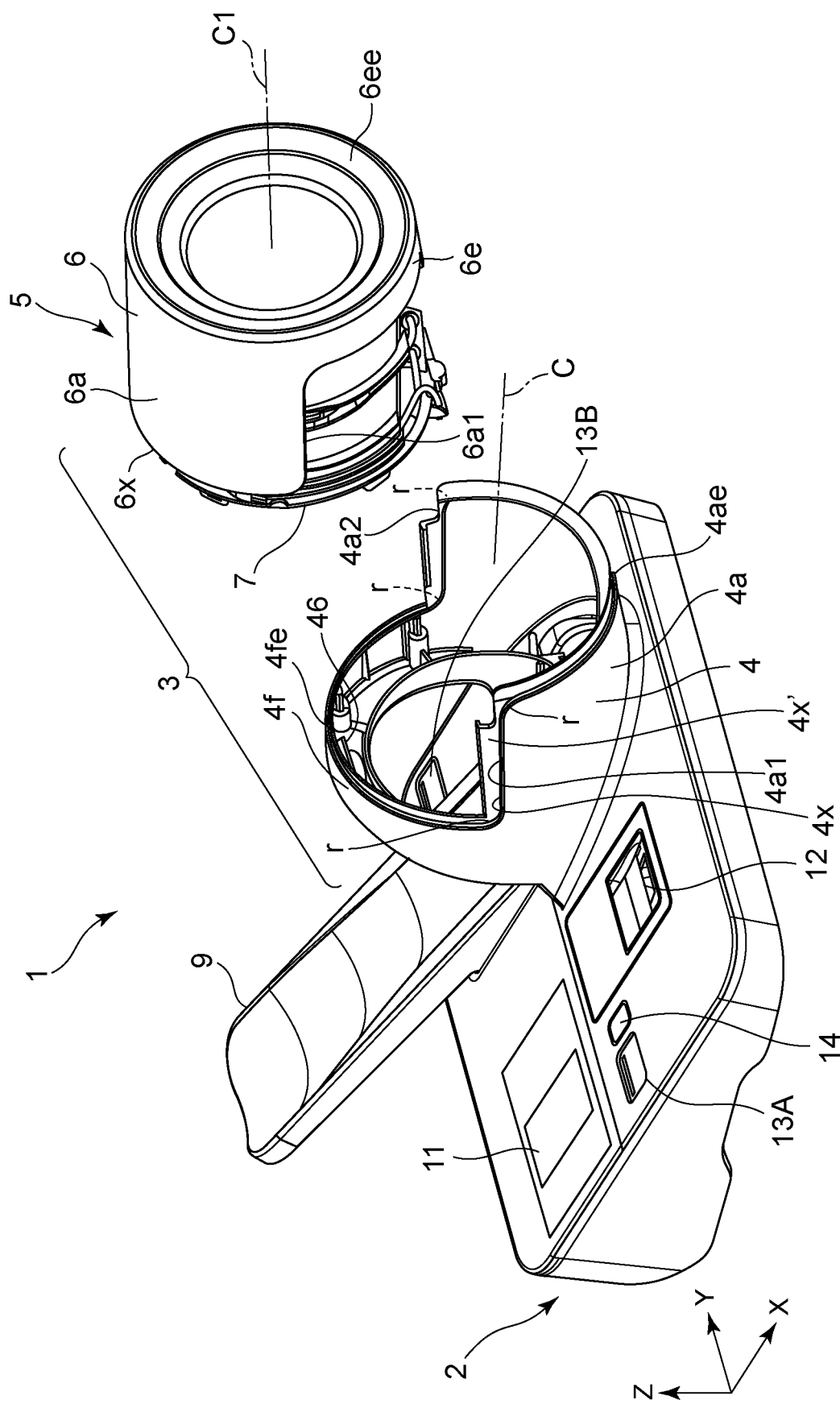
FIG. 4 is a diagram showing a state in which a main body and a cuff unit constituting the sphygmomanometer are separated from each other.

As shown in FIG. 4, the slide receiving part 4 integrally includes a front surface side portion 4a having a circular-arc (in this example, semi-circular) cross section that opens upward, and a rear surface side portion 4f connected to the rear of the front surface side portion 4a and having a circular cross-section concentric (about central axis C) with the circular-arc cross section of the front surface side portion 4a. In this example, the slide receiving part 4 is made of acrylonitrile-butadiene-styrene (ABS) resin.

A front edge 4ae of the front surface side portion 4a has a semicircular shape that opens upward in this example. Upper edges 4a1 and 4a2 on both sides of the front surface side portion 4a are substantially linear. A front edge 4fe of the rear surface side portion 4f has a semicircular shape that opens downward in this example. In the front surface side portion 4a, left and right upper ends of the front edge 4ae are connected to front ends of the upper edges 4a1 and 4a2 on both sides, respectively, while interposing a radius (a portion provided with a curvature) r. Further, left and right lower ends of the front edge 4fe of the rear surface side portion 4f are connected to rear ends of the upper edges 4a1 and 4a2 on both sides, respectively, while interposing the radius r. As a result, a boundary 4x of the slide receiving part 4 with respect to the cuff unit 5 (cover 6 described later) forms one continuous annular line. Note that the slide receiving part 4 is provided with a margin 4x' for the cuff unit 5 along the boundary 4x.

The slide receiving part 4 (the front surface side portion 4a thereof) is adapted to slidably receive the cuff unit 5 along the central axis C (extending in the direction perpendicular to the circular-arc cross section of the front surface side portion 4a). In this example, the slide receiving part 4 is tilted in a manner of gradually decreasing in height (decreasing in Z coordinate) toward a slide end A1f side in sliding directions A1 and A2 (see FIG. 3) in which the cuff unit 5 is slid. Thereby, the tilt of the cuff 3 described above is realized.

In this example, the slide receiving part 4 is rotatably attached to the main body 2 at a lower part on the slide end A1f side within a predetermined angular range (for example, a range of 0° to about 40° in the horizontal direction) by a not-shown hinge (a rotating shaft). As a result, the subject who is to perform the blood pressure measured can adjust the tilt angle of the slide receiving part 4, and thus the tilt angle of the cuff 3, in accordance with one's body size.

An h-shaped protrusion 46 forming a part of a lock part L is provided inside the upper part of the rear surface side portion 4f of the slide receiving part 4. The lock part L is described later with reference to FIGS. 9A and 9B.

Figure 12:
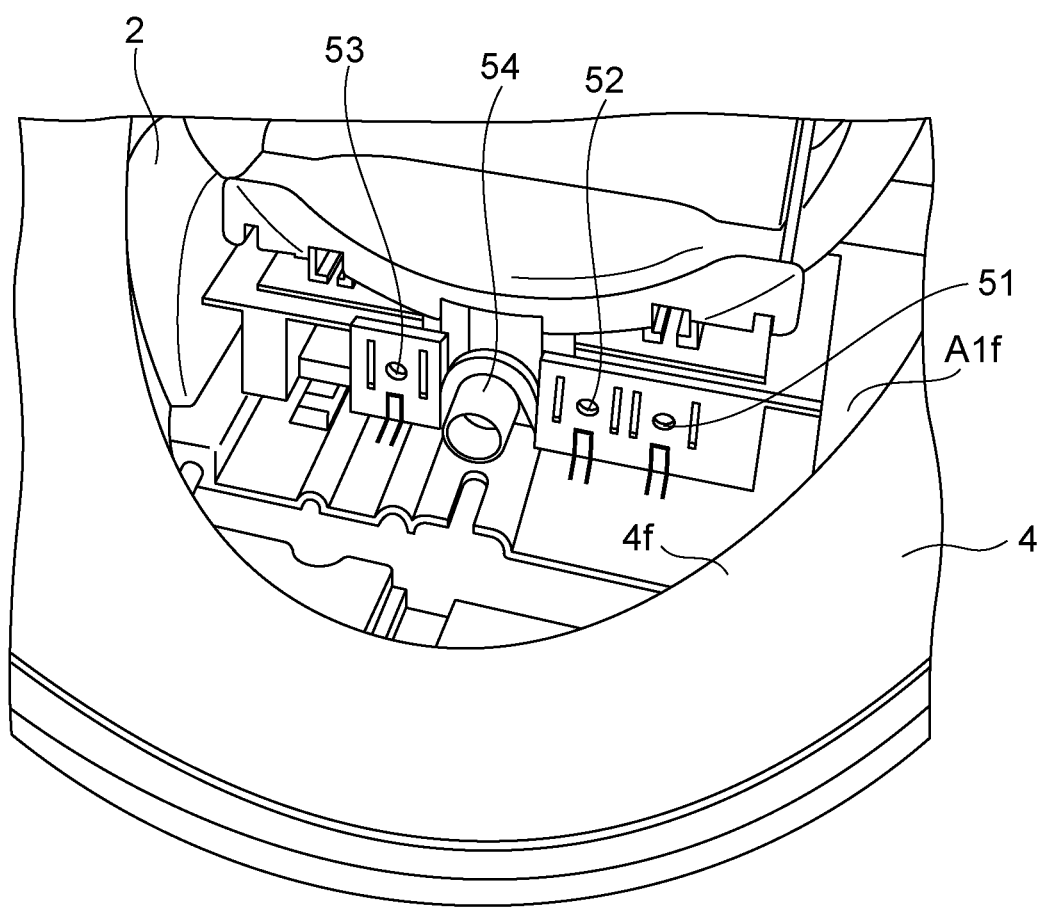
FIG. 12 is a diagram showing a first fluid connector provided at a portion of the main body corresponding to the slide end side of the slide receiving part.

Further, as shown in FIG. 12, female fluid connectors 51, 52, and 53 as first fluid connectors are provided side by side at a portion of the slide receiving part 4 corresponding to the slide end A1f side. These fluid connectors 51, 52, and 53 are in communication with a pump described later provided in the main body 2 via a not-shown flexible air tube at the rear. To these fluid connectors 51, 52, and 53, fluid connectors 81, 82, and 83 (see FIG. 6) of the cuff unit 5 which are described later are correspondingly connected from the front. As shown in FIG. 12, at a portion corresponding to a space between the fluid connector 52 and the fluid connector 53, a cylindrical protrusion 54 for positioning the cuff unit 5 with respect to the slide receiving part 4 is provided so as to protrude forward.

(Cuff Unit)

Figure 5:
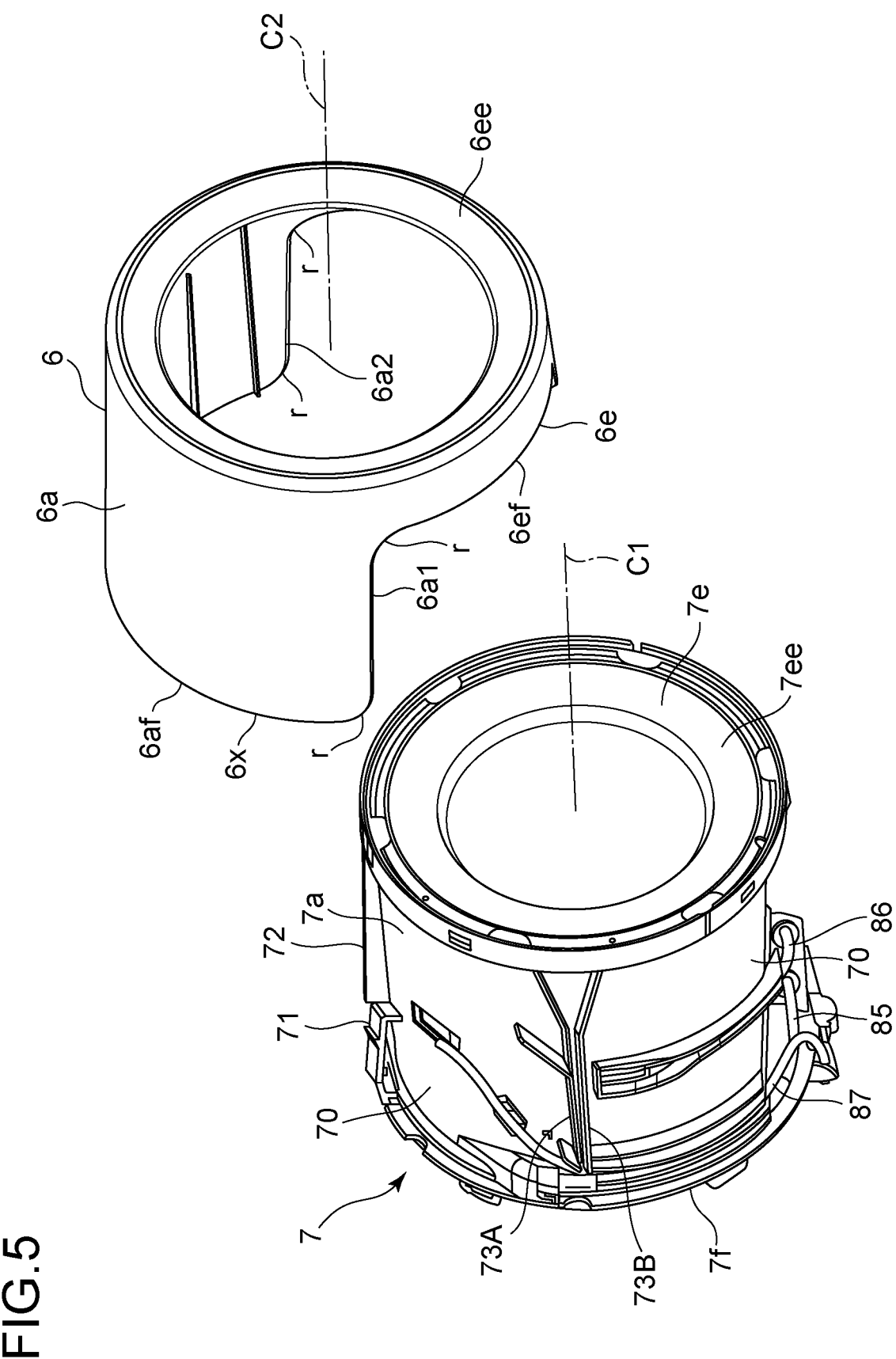
FIG. 5 is a diagram showing a state in which a cuff structure and a cover constituting the cuff unit are separated from each other.

As shown in FIG. 5, the cuff unit 5 is constituted of a cuff structure 7 having a cylindrical shape into which the upper arm 90 is inserted, and a cover 6 detachably attached integrally with the cuff structure 7.

Figure 8A:
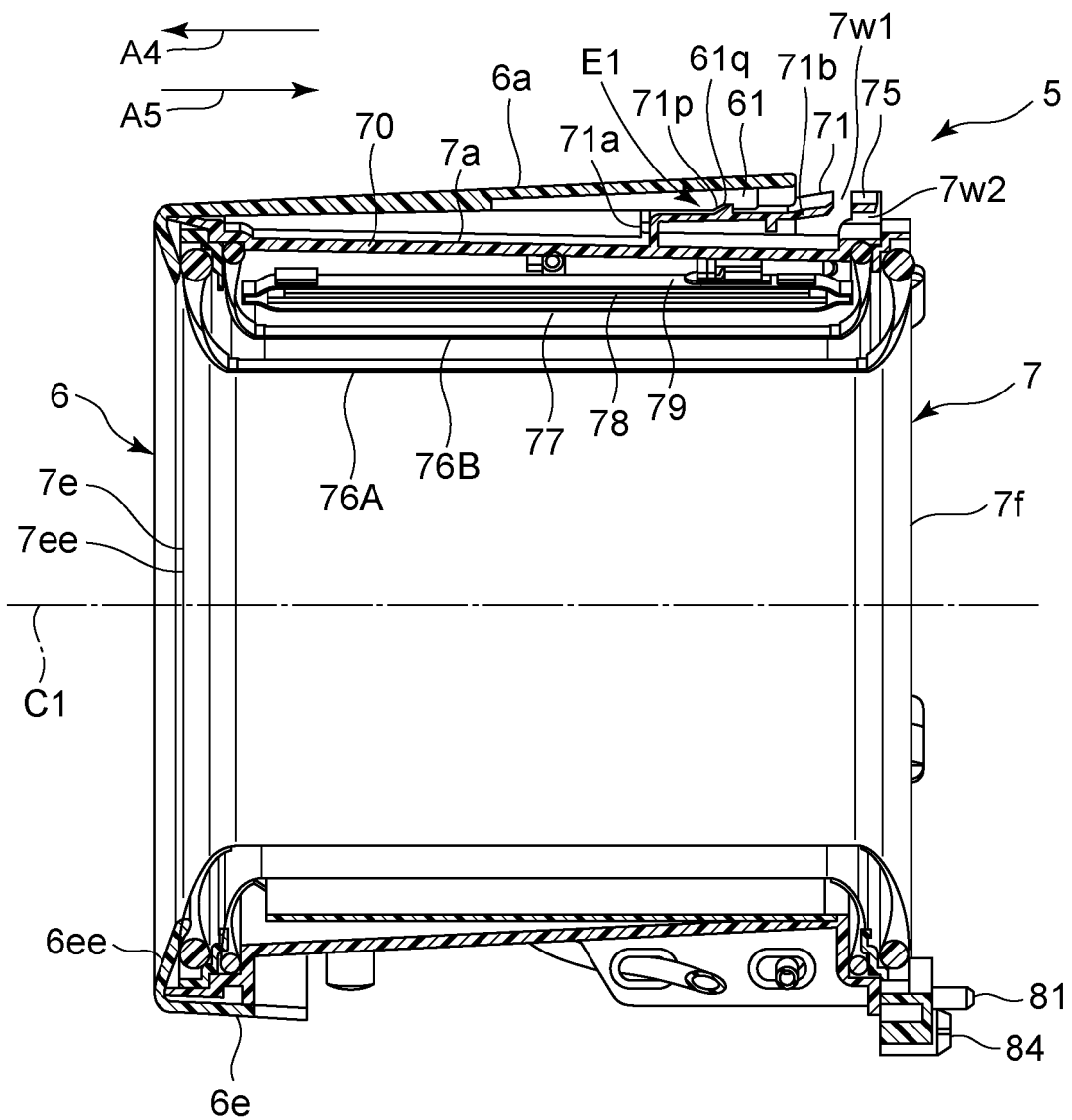
FIG. 8A is a diagram showing a cross section obtained when the cuff unit is cut along the central axis.

The cuff structure 7 includes a base member 70 formed of plastic material (for example, polyvinyl chloride) having a cylindrical shape. As shown in FIG. 8A (showing a cross section along a central axis C1 of the cuff unit 5), along the inner circumferential surface of the base member 70, a curler wrapping air bag 79, a curler 78, a measuring air bag 77, an inner cover 76B, and an outer cover 76A are sequentially provided. In this example, the curler wrapping air bag 79 and the measuring air bag 77 correspond to fluid bags.

The outer cover 76A is made of a cylindrical stretchable cloth having not-shown folds. The inner cover 76B is made of cushion material (for example, foam sponge material) having a cylindrical shape and a larger thickness than the outer cover 76A to prevent the upper arm 90 from being hurt during measurement. The outer cover 76A and the inner cover 76B are detachable from the base member 70. For example, when being stained, the outer cover 76A may be removed, washed, and then attached again.

Figure 14A:
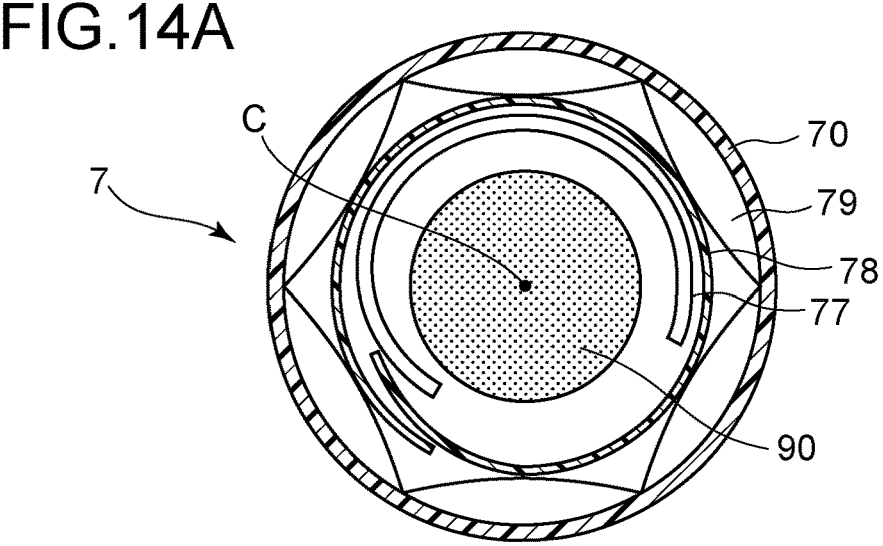
FIGS. 14A-14C are diagrams showing an operation of the cuff structure during blood pressure measurement.

The curler wrapping air bag 79 is made of a stretchable resin (for example, polyurethane). As shown in FIG. 14A (showing a cross section perpendicular to the central axis C of the cuff 3, that is, a cross section of the cuff unit 5 attached to the main body 2, which is perpendicular to the central axis C1), in this example, the curler wrapping air bag 79 is provided along the inner circumferential surface of the base member 70 while being divided in six sections.

The curler 78 is made of a resin having an appropriate flexibility (for example, polypropylene), and is produced to have a flat plate shape in the developed state, but have a substantially annular shape surrounding the upper arm 90 in the state of FIG. 14A (natural state), and such that the end portions in the circumferential direction overlap with each other.

The measuring air bag 77 is made of a stretchable resin (for example, polyurethane), similarly to the curler wrapping air bag 79. This measuring air bag 77 is set to a length (circumferential dimension) such that substantially two-thirds or more of the upper arm 90 along the inner circumferential surface of the curler 78 can be wrapped. (However, in the state of FIG. 14A, the circumferential ends of the measuring air bag 77 are relatively far apart from each other.)

Figure 6:
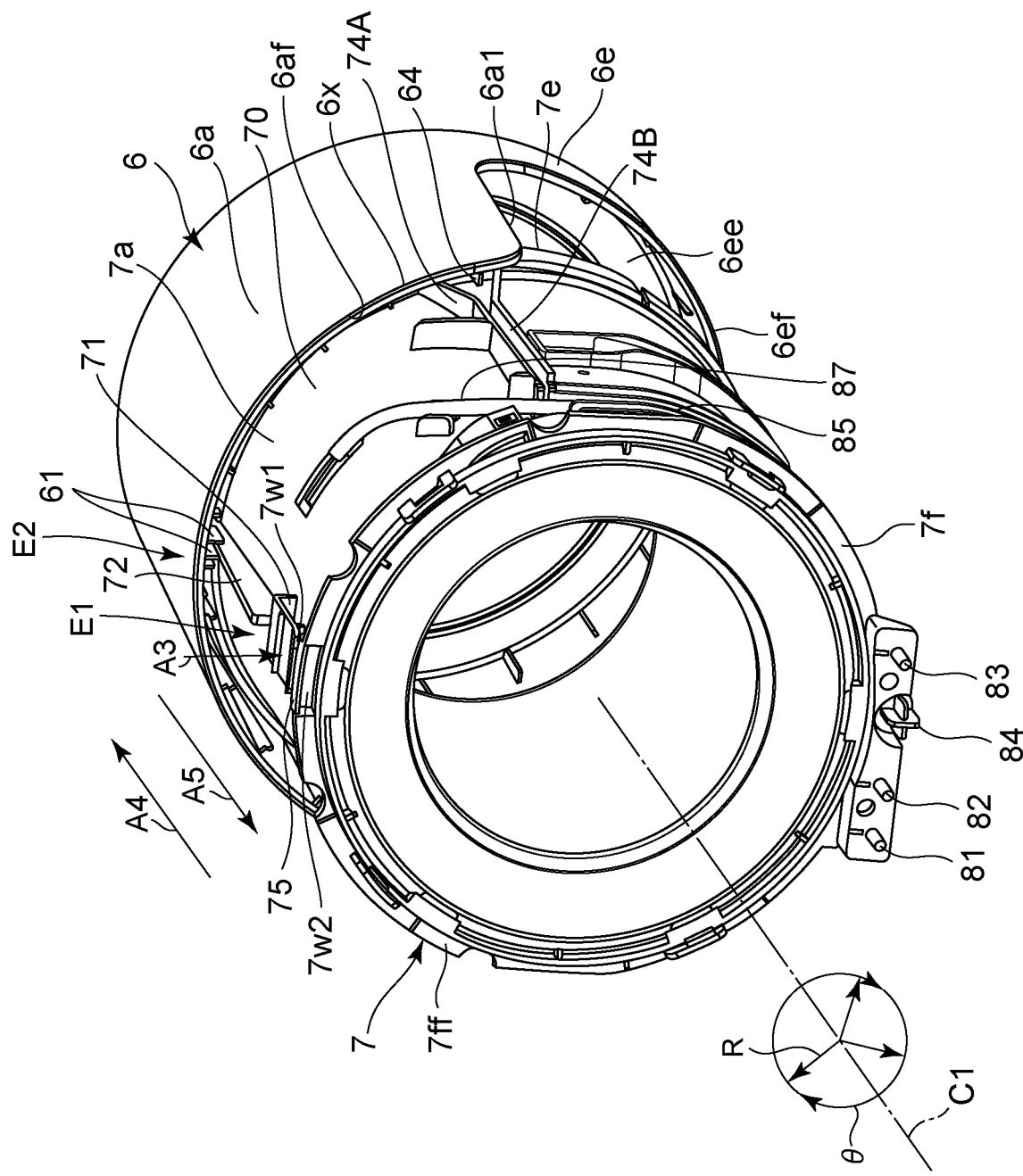
FIG. 6 is a diagram illustrating a method of attaching and detaching the cover to and from the cuff structure.

As shown in FIG. 6, the male fluid connectors 81, 82, and 83 as second fluid connectors are provided side by side in the lower part on a rear surface 7f side of the cuff structure 7. The fluid connector 81 communicates with the measuring air bag 77 via an air tube 85 arranged along an outer circumferential surface 7a of the base member 70. The fluid connectors 82 and 83 communicate with the curler wrapping air bag 79 via air tubes 86 and 87 (see FIG. 5) arranged along the outer circumferential surface 7a of the base member 70. As shown in FIG. 6, at a portion corresponding to a space between the fluid connector 82 and the fluid connector 83, a cross-shaped protrusion 84 for positioning the cuff unit 5 with respect to the main body 2 is provided so as to protrude rearward.

As shown in FIGS. 5 and 6, the cuff structure 7 (base member 70) is provided with, at the upper part on the outer circumferential surface 7a thereof, an L-shaped protrusion 71 forming a part of a first engagement part E1 for locking the cuff structure 7 with the cover 6 in the axial direction of the cuff structure 7 (the direction in which the central axis C1 extends). As shown in FIG. 8A, the L-shaped protrusion 71 includes a substantially rectangular protruding plate part 71a erected radially outward on the outer circumferential surface 7a of the base member 70, and a substantially rectangular parallel plate part 71b extending from the tip end of the protruding plate part 71a to the rear surface 7f side substantially along the axial direction. On an outer surface (the surface facing the cover 6) 71u of the parallel plate part 71b, an engaging projection 71p protruding radially outward is provided. As shown in an enlarged view in FIG. 8B, the engaging projection 71p includes a tilted surface 71p1 that is tilted in a manner of gradually increasing in height from the level of the outer surface 71u from the front surface 7e side toward the rear surface 7f side, and a vertical surface 71p2 that radially connects the top of the tilted surface 71p1 with the level of the outer surface 71u. Additionally, on an inner surface (surface facing the base member 70) 71v of the parallel plate part 71b, a restricting protrusion 71s protruding radially inward is provided. The restricting protrusion 71s is provided to restrict the parallel plate part 71b from flexing radially inward to the extent necessary and sufficient to lock or unlock the cuff structure 7 and the cover 6.

Further, as shown in FIGS. 5 and 6, the cuff structure 7 is provided with, at the upper part on the outer circumferential surface 7a thereof, a rib 72 forming a part of a second engagement part E2 (see FIG. 6) for restricting relative movement between the cuff structure 7 and the cover 6 in the radial direction R and the circumferential direction θ of the cuff structure 7. The rib 72 has a plate shape protruding radially outward. Further, among the outer circumferential surface 7a of the cuff structure 7, there is provided on the left side part when viewed from the front surface 7e side (see FIG. 5), a pair of upper and lower guide ribs 73A and 73B forming a part of the second engagement part E2 so as to protrude radially outward. A vertical gap between the guide ribs 73A and 73B gradually decrease from the front surface 7e side toward the rear surface 7f side in a front half part and is constant in a rear half part. Similarly, among the outer circumferential surface 7a of the cuff structure 7, there is provided on the right side part when viewed from the front surface 7e side (see FIG. 6), a pair of upper and lower guide ribs 74A and 74B forming a part of the second engagement part E2 so as to protrude radially outward. A vertical gap between the guide ribs 74A and 74B gradually decrease from the front surface 7e side toward the rear surface 7f side in the front half part and is constant in the rear half part.

As shown in FIGS. 5 and 6, the cover 6 integrally includes a rear surface side portion 6a having a circular-arc (in this example, a semicircular) cross section that opens downward, and a front surface side portion 6e (portion on the side facing the subject) connected to the front of the rear surface side portion 6a and having a circular cross-section concentric (about a central axis C2 shown in FIG. 5) with the circular-arc cross section of the rear surface side portion 6a. Similarly to the slide receiving part 4, the cover 6 is made of ABS resin in this example.

A rear edge 6af of the rear surface side portion 6a has a semicircular shape that opens downward in this example. Lower edges 6a1 and 6a2 on both sides of the rear surface side portion 6a are substantially linear. A rear edge 6ef of the front surface side portion 6e has a semicircular shape that opens upward in this example. In the rear surface side portion 6a, left and right upper ends of the rear edge 6af and the rear ends of the lower edges 6a1 and 6a2 on both sides are connected, respectively while interposing the radius r. Further, In the front surface side portion 6e, left and right upper ends of the rear edge 6ef and the front ends of the lower edges 6a1 and 6a2 on both sides are connected, respectively while interposing the radius r. As a result, a boundary 6x of the cover 6 with respect to the slide receiving part 4 forms one continuous annular line that matches the boundary 4x of the slide receiving part 4. Therefore, in a state where the sphygmomanometer 1 is set up as shown in FIGS. 1 to 3, a gap is not generated between the cover 6 and the slide receiving part 4.

In this example, the front surface side portion 6e of the cover 6, in particular, an end surface 6ee on the front surface side arranged to face the subject during blood pressure measurement forms an annular shape so as to cover an end surface 7ee on the front surface side of the cuff structure 7. Therefore, for example, in a state in which the sphygmomanometer 1 is set up as shown in FIG. 1, the cuff structure 7 is covered by the cover 6 and the slide receiving part 4, and particularly, the end surface 7ee on the front side of the cuff structure 7 is covered by the end surface 6ee on the front surface side of the cover 6. Therefore, even if the cuff structure 7 is replaced due to defects, for example, the user cannot recognize from the appearance in the set-up state that the cuff structure 7 has been replaced. Therefore, the user is prevented from feeling odd.

Figure 7:
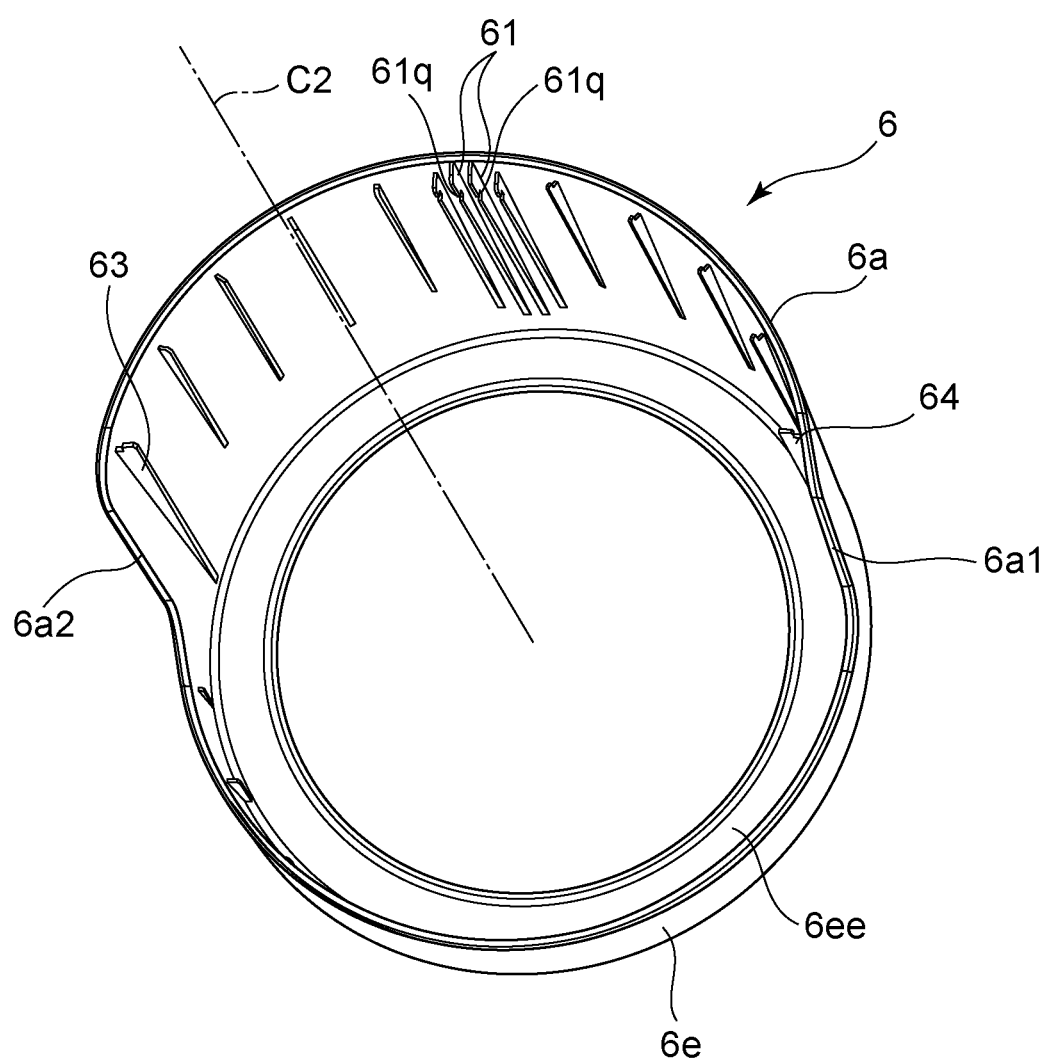
FIG. 7 is a diagram showing the inside of the cover.

As shown in FIG. 7, a plurality of ribs 61, 61, 63, 64, . . . , along the axial direction (the direction in which the central axis C2 extends) is provided on the inner circumferential surface of the cover 6. These ribs 61, 61, 63, 64, . . . , have a plate shape protruding radially inward.

A pair of parallel ribs 61 and 61 provided at the upper part of the inner circumferential surface of the cover 6 is designed so as to form a part of the first engagement part E1 for locking the cuff structure 7 with the cover 6, and so as to form a part of the second engagement part E2 for restricting the relative movement between the cuff structure 7 and the cover 6 in the radial direction R and the circumferential direction θ of the cuff structure 7. Further, the ribs 64 and 63 provided on the left and right side parts of the inner circumferential surface of the cover 6 are also designed so as to form a part of the second engagement part E2 for restricting the relative movement between the cuff structure 7 and the cover 6 in the radial direction R and the circumferential direction θ of the cuff structure 7.

Figure 8B:
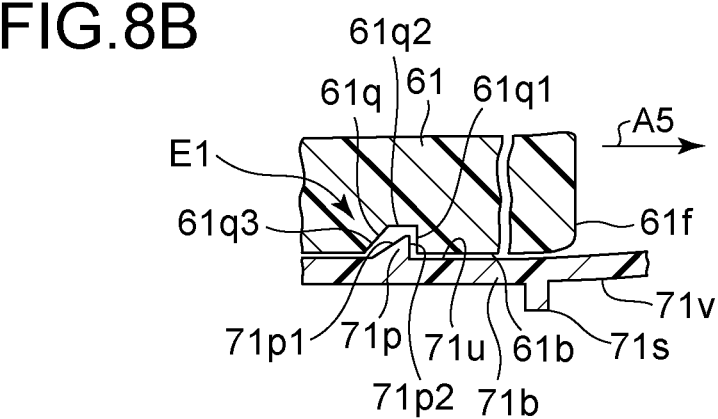
FIG. 8B is an enlarged diagram of a first engagement part of FIG. 8A that engages the cuff structure with the cover.

Specifically, as shown in an enlarged manner in FIG. 8B, a ridge surface 61b of each rib 61 is provided with an engaging recession 61q that is recessed radially outward, at a position corresponding (in the state of the cover 6 being attached to the cuff structure 7) to the engaging projection 71p of the L-shaped protrusion 71 of the cuff structure 7 described above. The engaging recession 61q includes a tilted surface 61q3 that is tilted from the front surface 7e side toward the rear surface 7f side in a manner of gradually recessing from the level of the ridge surface 61b, a bottom surface 61q2 that is continuous with the tilted surface 61q3 and is substantially parallel to the ridge surface 61b, and a vertical surface 61q1 radially connecting the level of the bottom surface 61q2 with the level of the ridge surface 61b. The size of the engaging recession 61q is set to a size capable of accommodating the engaging projection 71p of the L-shaped protrusion 71.

When the cover 6 is slid from the front surface 7e side toward the rear surface 7f side along the upper half of the outer circumferential surface 7a of the cuff structure 7 in the direction indicated by an arrow A5 in FIGS. 6 and 8A, the rib 61 slides with respect to the L-shaped protrusion 71 as shown in an enlarged manner in FIG. 8B. At this time, first, the tilted surface 71p1 of the engaging projection 71p abuts with a rear end 61f of the rib 61, and the parallel plate part 71b of the L-shaped protrusion 71 flexes radially inward. Further, when the rib 61 is slid with respect to the L-shaped protrusion 71 in the direction indicated by the arrow A5 while the ridge surface 61b of the rib 61 rubs the top of the engaging projection 71p, the vertical surface 71p2 of the engaging projection 71p of the L-shaped protrusion 71 passes the vertical surface 61q1 of the engaging recession 61q of the rib 61. As a result, the engaging projection 71p is accommodated in the engaging recession 61q and functions as the first engagement part E1, and thereby the cover 6 is detachably engaged and locked in the axial direction of the cuff structure 7. At this time, because the shapes of the vertical surface 61q1 and the vertical surface 71p2 are perpendicular to the sliding direction, the flexure of the parallel plate part 71b of the L-shaped protrusion 71 is suddenly eliminated. As a result, the outer surface 71u of the parallel plate part 71b of the L-shaped protrusion 71 that tries to return to the natural state collides with the ridge surface 61b of the rib 61, and a "clicking" sound indicating the completion of locking is generated. Therefore, the service person, etc. can know that the cover 6 is correctly attached to the cuff structure 7 by listening to the "clicking" sound from the first engagement part E1. As a result, the service person, etc. can surely proceed with the setup of this sphygmomanometer 1.

Further, when the cover 6 is slid along the upper half of the outer circumferential surface 7a of the cuff structure 7 from the front surface 7e side toward the rear surface 7f side in the direction indicated by the arrow A5 in FIG. 6, the rib 72 provided on the outer circumferential surface 7a of the cuff structure 7 enters the gap between the pair of ribs 61 and 61 provided at the upper part of the inner circumferential surface of the cover 6. Along with this, the ribs 64 and 63 (see FIG. 6) provided on the left and right sides on the inner circumferential surface of the cover 6 enter the gap between the pair of upper and lower guide ribs 74A and 74B provided on the left side part (as viewed from the front surface 7e side) of the outer circumferential surface 7a of the cuff structure 7, and the gap between the pair of upper and lower guide ribs 73A and 73B provided on the right side part (see FIG. 5), respectively. As a result, the second engagement part E2 functions to restrict the relative movement between the cuff structure 7 and the cover 6 in the radial direction R and the circumferential direction θ of the cuff structure 7. Here, as described above, the vertical gap between the pair of guide ribs 74A and 74B gradually decreases from the front surface 7e side toward the rear surface 7f side in the front half part and is constant in the rear half part. Similarly, the vertical gap between the pair of guide ribs 73A and 73B gradually decreases from the front surface 7e side toward the rear surface 7f side in the front half part and is constant in the rear half part. Therefore, the pair of guide ribs 74A and 74B and the pair of guide ribs 73A and 73B can smoothly guide and accommodate the ribs 64 and 63 in the gaps, respectively.

As a result, the service person, etc. can detachably attach the cover 6 to the cuff structure 7 integrally even with the simple operation of sliding the cover 6 along the upper half of the outer circumferential surface 7a of the cuff structure 7, to allow the cuff unit 5 to be integrally constituted.

Conversely, when the cover 6 is detached from the cuff structure 7, a rear part of the parallel plate part 71b of the L-shaped protrusion 71 (indicating a portion protruding farther in the rear than the rear end 61f of the rib 61 shown in FIG. 8B, and hereinafter, this is referred to as the "rear part of the L-shaped protrusion 71") is pressed in the direction indicated by an arrow A3 in FIG. 6 (radially inward). As a result, the engaging projection 71p comes out from the engaging recession 61q shown in FIG. 8B, and the axial locking by the first engagement part E1 is released. Then, in the state of the locking being released, the cover 6 is slid in the direction shown by an arrow A4 in FIGS. 6 and 8A along the upper half of the outer circumferential surface 7a of the cuff structure 7, from the rear surface 7f side toward the front surface 7e side. Then, the rib 72 comes out of the gap between the ribs 61 and 61, and the ribs 64 and 63 come out of the gap between the guide ribs 74A and 74B and the gap between the guide ribs 73A and 73B, respectively, and the restriction in relative movement by the second engagement part E2 in the radial direction R and the circumferential direction θ is released. As a result, the cover 6 is detached from the cuff structure 7 as shown in FIG. 5.

(Attachment and Detachment of the Cuff Unit to and from the Main Body)

As shown in FIGS. 6 and 8A, the cuff structure 7 (base member 70) is provided with, at the upper part on the rear surface 7f side, a horizontal bar part 75 having a substantially rectangular cross section and forming a part of the lock part L described later. The horizontal bar part 75 is supported by an annular flange part 7ff (see FIG. 6) provided on the rear surface 7f side of the cuff structure 7. An axial gap 7w1 is provided between the horizontal bar part 75 and the L-shaped protrusion 71 (the parallel plate part 71b thereof). Further, a radial gap 7w2 is formed between the horizontal bar part 75 and the outer circumferential surface 7a of the base member 70 that allows (a movable plate part 46b of) the h-shaped protrusion 46 described below to pass through.

As shown in FIG. 9A, the h-shaped protrusion 46 forming a part of the lock part L is provided inside the upper part of the rear surface side portion 4f of the slide receiving part 4. The h-shaped protrusion 46 is generally provided so as to be tilted along the sliding directions A1 and A2 along which the cuff unit 5 is slid. As shown in an enlarged manner in FIG. 9B, the h-shaped protrusion 46 includes a movable plate part 46b provided along the central axis C (sliding directions A1 and A2) of the slide receiving part 4, the vertical plate part 46d extending radially outward from a substantially center (in FIG. 9B) 46c of an upper surface 46u of the movable plate part 46b, and a support plate part 46a that supports an upper end of the vertical plate part 46d. The support plate part 46a is constituted of a part of the rear surface side portion 4f of the slide receiving part 4, and a position and a posture thereof are maintained with respect to other portions of the rear surface side portion 4f (portions other than the h-shaped protrusion 46). The movable plate part 46b is supported only by the vertical plate part 46d, and the vertical plate part 46d is supported only by the support plate part 46a. In addition, an engaging projection 46p protruding radially outward is provided at the front end of the movable plate part 46b. The engaging projection 46p includes a tilted surface 46p1 tilted in a manner of gradually increasing in height from the front to the rear, and a vertical surface 46p2 radially connecting the top of the tilted surface 46p1 with the level of the upper surface 46u. The axial distance between the engaging projection 46p and the vertical plate part 46d is set slightly larger than the axial dimension of the horizontal bar part 75 so that the horizontal bar part 75 can be accommodated.

Figure 11:
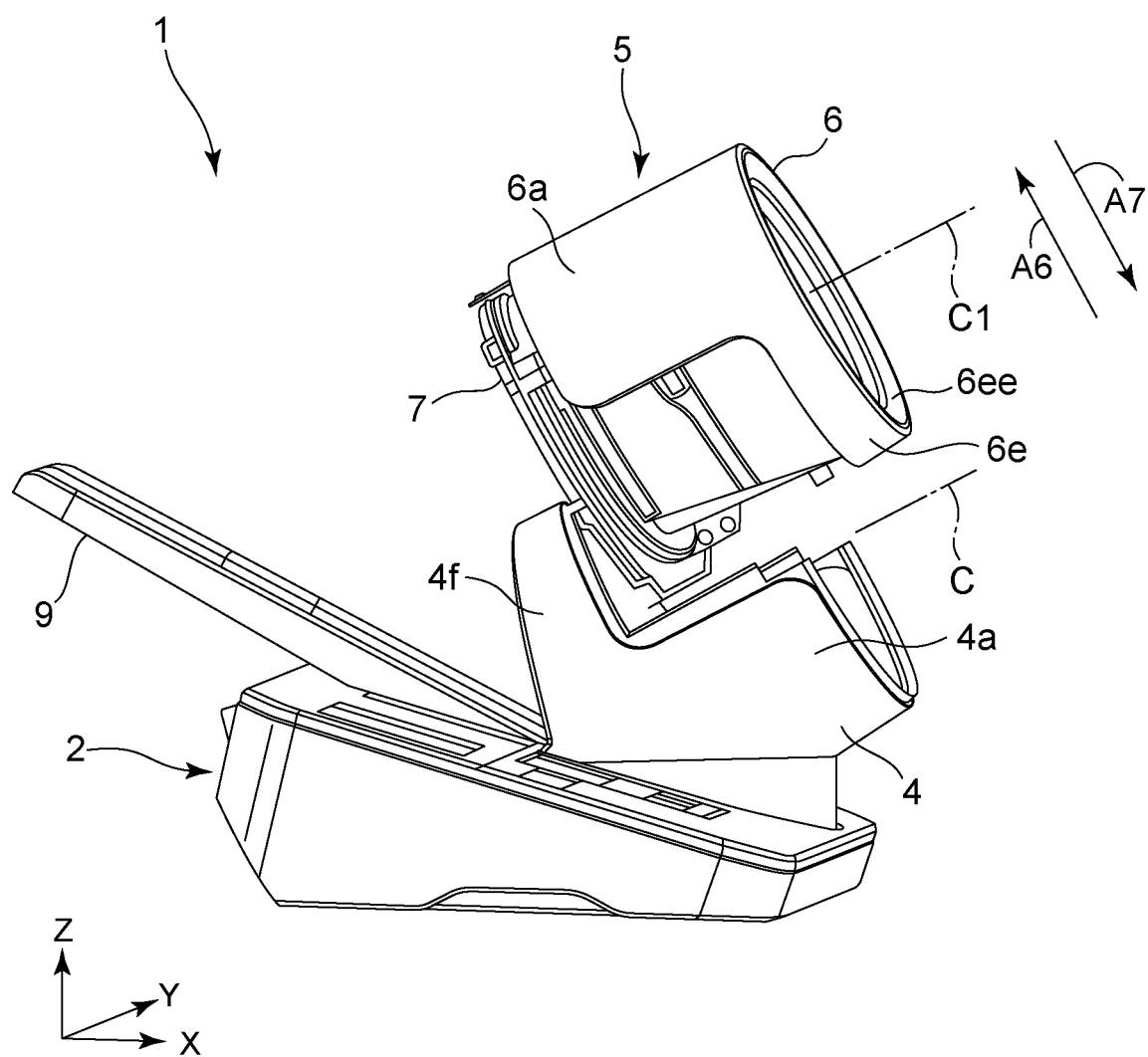
FIG. 11 is a diagram illustrating a method of detaching the cuff unit from (the slide receiving part of) the main body.

When the cuff unit 5 is attached to the main body 2 (slide receiving part 4), first, the cuff unit 5 is placed on the slide receiving part 4 of the main body 2 as indicated by an arrow A7 in FIG. 11. Next, when the cuff unit 5 is slid along the central axis C of the slide receiving part 4 in the direction indicated by the arrow A1 in FIG. 9A (that is, toward the slide end A1f side), a corner formed by an inner surface 75b and the rear end surface 75f of the horizontal bar part 75 shown in FIG. 9B abuts with the tilted surface 46p1 of the engaging projection 46p of the h-shaped protrusion 46, and the movable plate part 46b and the vertical plate part 46d of the h-shaped protrusion 46 flex to cause the engaging projection 46p to be displaced radially inward. Furthermore, when the horizontal bar part 75 is slid with respect to the h-shaped protrusion 46 in the direction indicated by the arrow A1 while the inner surface 75b of the horizontal bar part 75 rubs the top of the engaging projection 46p, a front end surface 75e of the horizontal bar part 75 passes the vertical surface 46p2 of the engaging projection 46p of the h-shaped protrusion 46. As a result, the engaging projection 46p is accommodated in the axial gap 7w1, and the horizontal bar part 75 is accommodated between the engaging projection 46p and the vertical plate part 46d to function as the lock part L, and thereby the cuff unit 5 is detachably engaged with and locked to the main body 2 (slide receiving part 4) in the axial direction. At this time, because the shapes of the front end surface 75e and the vertical surface 46p2 are perpendicular to the sliding direction, the flexure of the movable plate part 46b and the vertical plate part 46d of the h-shaped protrusion 46 is suddenly eliminated. As a result, the upper surface 46u (the portion in front of the substantially center 46c) of the movable plate part 46b of the h-shaped protrusion 46 that tries to return to the natural state collides with the inner surface 75b of the horizontal bar part 75, and the "clicking" sound indicating the completion of locking is generated. Therefore, the service person, etc. can know that the cuff unit 5 is correctly attached to the main body 2 by listening to the "clicking" sound of the lock part L. As a result, the service person, etc. can surely proceed with the setup of this sphygmomanometer 1.

Figure 10A:
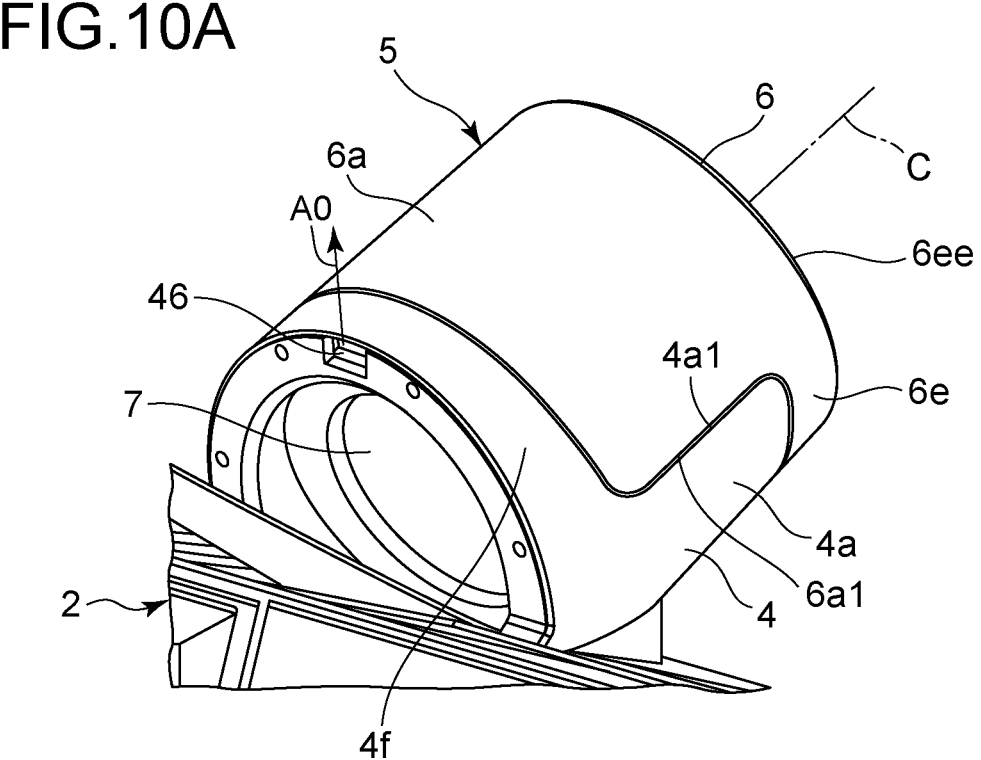
FIG. 10A is a diagram showing a state in which the cuff unit is attached to a slide receiving part of the main body.
Figure 10B:
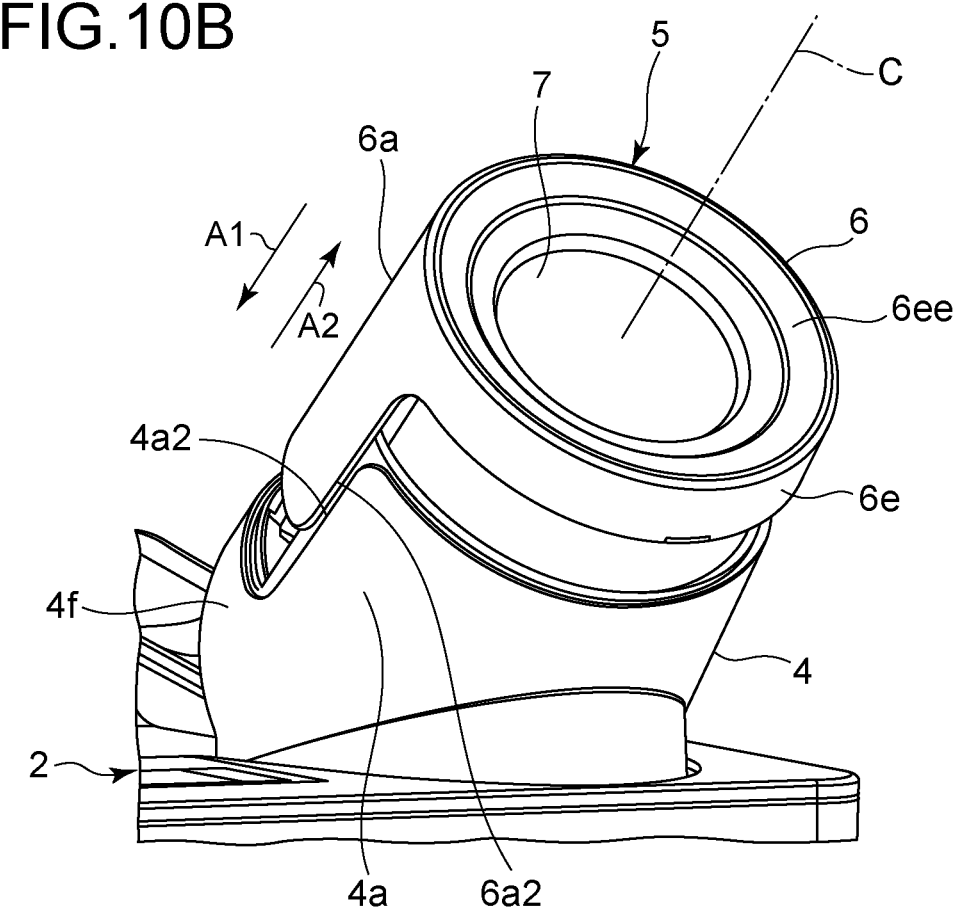
FIG. 10B is a diagram illustrating a method of detaching the cuff unit from the slide receiving part.

At this time, for example, the upper edges 4a1 and 4a2 on both sides of the front surface side portion (having the circular-arc cross section that opens upward) 4a of the slide receiving part 4 shown in FIGS. 10A and 10B abut with the lower edges 6a1 and 6a2 on both sides of the rear surface side portion (having the circular-arc cross section that opens downward) 6a of the cover 6 to support the weight of the cuff unit 5 (in this example, about 1 kg). Therefore, for example, the service person, etc. who sets up this sphygmomanometer 1 does not need to support the weight of the cuff unit 5 with one's own hand when sliding the cuff unit 5, and can easily attach the cuff unit 5 only by pushing (sliding) the cuff unit 5 toward the slide end A1f side. In particular, in this example, the slide receiving part 4 is tilted in the manner of gradually decreasing in height toward the slide end A1f side. Therefore, the service person, etc. can use the gravity applied to the cuff unit 5, and can therefore attach the cuff unit 5 more easily.

Further, when the cuff unit 5 is attached by being slid along the slide receiving part 4 toward the slide end A1f side, the cross-shaped protrusion 84 (see FIG. 6) provided at the lower part of the rear surface 7f side of the cuff unit 5 (cuff structure 7) fits into the cylindrical protrusion 54 (see FIG. 12) provided at the portion corresponding to the slide end A1f side of the slide receiving part 4 of the main body 2. As a result, the cuff unit 5 is positioned in the radial direction of the slide receiving part 4. Along with this, the fluid connectors 81, 82, and 83 (see FIG. 6) provided at the lower part on the rear surface 7f side of the cuff unit 5 (cuff structure 7) are connected to the fluid connectors 51, 52, and 53 (see FIG. 12) provided at the portions corresponding to the slide end A1*f* side of the slide receiving part 4 of the main body 2 by fitting in fluid flowable and detachably attached manners.

Therefore, the service person, etc. can easily set up this sphygmomanometer 1. That is, the service person, etc. can detachably attach the cuff unit 5 to the main body 2 (slide receiving part 4) to allow this sphygmomanometer 1 to be integrally constituted with the simple operation.

The sphygmomanometer 1 set up in this way is in the attached state in which the cylindrical cuff unit 5 is received by the slide receiving part 4 having the circular-arc cross section that opens upward. Therefore, the external force in the direction perpendicular to the sliding directions A1 and A2 is hardly applied between the slide receiving part 4 and the cuff unit 5, and twisting hardly occurs. Therefore, the reliability of the fluid flowable connection between the fluid connectors 51, 52, and 53 and the fluid connectors 81, 82, and 83 is enhanced.

Conversely, when the cuff unit 5 is detached from the main body 2 (slide receiving part 4), the rear part of the h-shaped protrusion 46 (indicating a portion on the rear of the substantially center 46*c* of the movable plate part 46*b* shown in FIG. 9B, and the same applies hereinafter) is pressed in the direction indicated by an arrow A0 in FIG. 10A (radially outward). As a result, the movable plate part 46*b* and the vertical plate part 46*d* (mainly the latter) of the h-shaped protrusion 46 shown in FIG. 9B flex to cause the engaging projection 46*p* to be displaced radially inward. As a result, the engaging projection 46*p* comes out from the gap 7*w*1, and the axial locking by the lock part L is released. Next, in the unlocked state, the cuff unit 5 is slid with respect to the slide receiving part 4 in the direction indicated by the arrow A2 in FIGS. 9A and 10B (opposite to the attaching direction). At this time, as in the case of attaching, the upper edges 4*a*1 and 4*a*2 on both sides of the front surface side portion 4*a* of the slide receiving part 4 abut with the lower edges 6*a*1 and 6*a*2 on both sides of the rear surface side portion 6*a* of the cover 6 to support the weight of the cuff unit 5. Therefore, the service person, etc. does not need to support the weight of the cuff unit 5 with one's own hand when sliding the cuff unit 5, and can slide the cuff unit 5 easily.

Further, when the cuff unit 5 is slid with respect to the slide receiving part 4 in the direction opposite to the attaching direction, the cross-shaped protrusion 84 (see FIG. 6) provided at the lower part on the rear surface 7*f* side of the cuff unit 5 (cuff structure 7) disengages from the cylindrical protrusion 54 (see FIG. 12) provided at the portion corresponding to the slide end A1*f* side of the slide receiving part 4 of the main body 2. Along with this, the fluid connectors 81, 82, and 83 (see FIG. 6) provided at the lower part on the rear surface 7*f* side of the cuff unit 5 (cuff structure 7) disengage from the fluid connectors 51, 52, and 53 (see FIG. 12) provided at the portion corresponding to the slide end A1*f* side of the slide receiving part 4 of the main body 2.

Thereafter, as shown by an arrow A6 in FIG. 11, the cuff unit 5 is lifted and detached from the main body 2 (slide receiving part 4).

In this way, the service person, etc. can easily disassemble this sphygmomanometer 1. That is, the service person, etc. can detach the cuff unit 5 from the main body 2 (slide receiving part 4) with the simple operation.

(Block Configuration of Control System)

Figure 15:
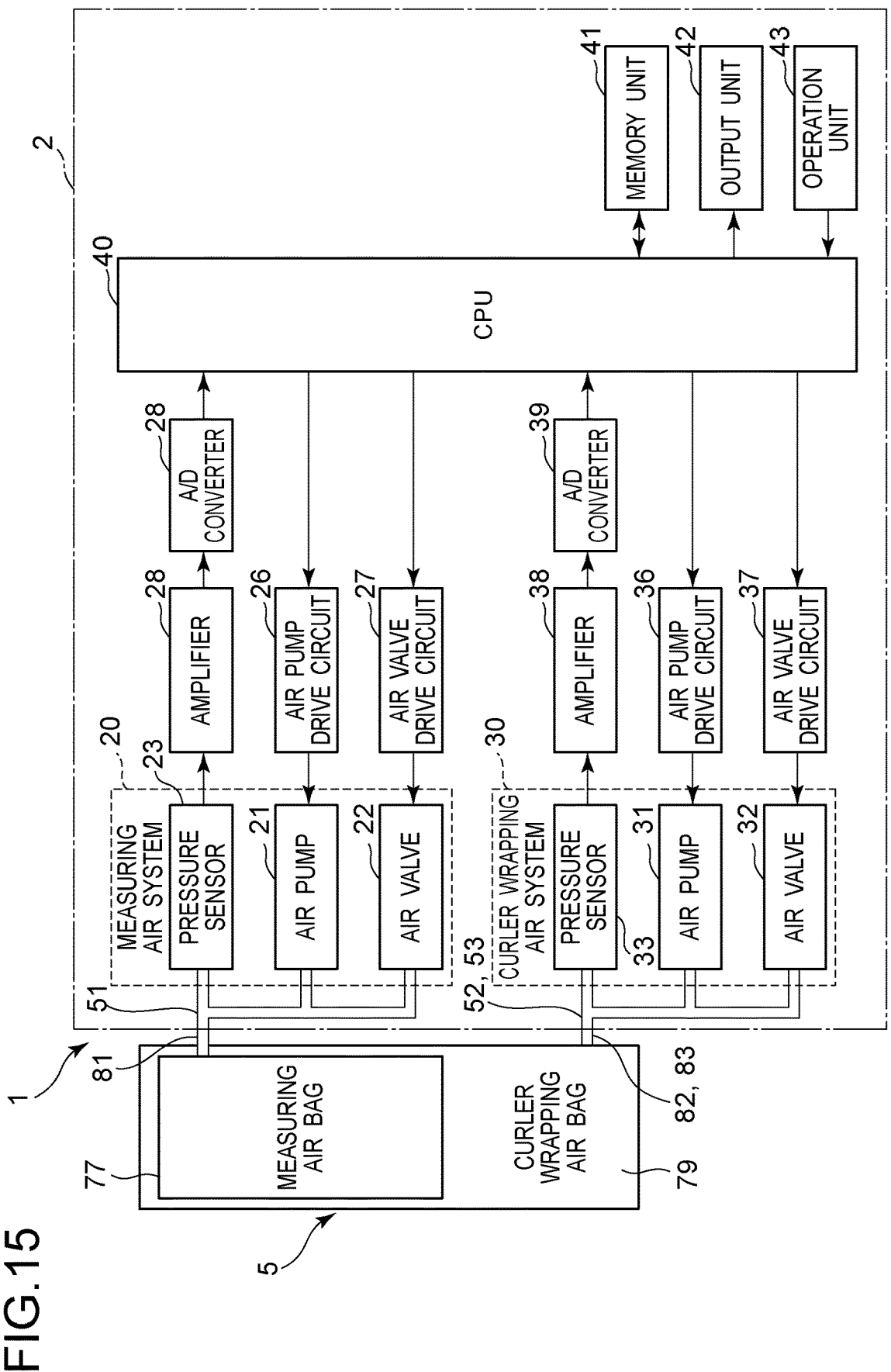
FIG. 15 is a diagram showing a block configuration of a control system of the sphygmomanometer in a state of the cuff unit being attached to the main body.

FIG. 15 shows a block configuration of a control system of the sphygmomanometer 1 in a state of the cuff unit 5 being attached to the main body 2. As shown in FIG. 15, the measuring air bag 77 in the cuff unit 5 is connected to a measuring air system 20 in the main body 2 via the fluid connectors 81 and 51. The curler wrapping air bag 79 in the cuff unit 5 is connected to a curler wrapping air system 30 in the main body 2 via the fluid connectors 82, 83, 52, and 53. The operations of the measuring air system 20 and the curler wrapping air system 30 are each controlled by a central processing unit (CPU) 40.

The measuring air system 20 includes an air pump 21, an air valve 22, and a pressure sensor 23. The air pump 21 is means for pressurizing inside of the measuring air bag 77, is driven by an air pump drive circuit 26 that receives a command from the CPU 40, and feeds the air as a fluid so that the pressure inside of the measuring air bag 77 becomes a predetermined pressure during measurement.

The air valve 22 is means for maintaining or reducing the pressure in the measuring air bag 77, and the open/closed state thereof is controlled by an air valve drive circuit 27 that receives a command from the CPU 40. The air value 22 also maintains or reduces the pressure in the measuring air bag 77 which is highly pressurized by the air pump 21 during measurement, and returns the pressure in the measuring air bag 77 to the atmospheric pressure after the measurement is completed.

The pressure sensor 23 is means for detecting the pressure in the measuring air bag 77, detects the pressure in the measuring air bag 77 that changes every moment during measurement, and outputs a signal according to the detected value to an amplifier 28. The amplifier 28 amplifies the signal output from the pressure sensor 23 and outputs the signal to an analog/digital (A/D) converter 29. The A/D converter 29 digitizes the analog signal output from the amplifier 28 and outputs the signal to the CPU 40.

The curler wrapping air system 30 includes an air pump 31, an air valve 32, and a pressure sensor 33. The air pump 31 is means for pressurizing inside of the curler wrapping air bag 79, is driven by an air pump drive circuit 36 that receives a command from the CPU 40, and feeds the air as a fluid so that the pressure inside the curler wrapping air bag 79 becomes a predetermined pressure at the start of measurement.

The air valve 32 is means for maintaining and reducing the pressure in the curler wrapping air bag 79, and the open/closed state thereof is controlled by an air valve drive circuit 37 that receives a command from the CPU 40. The air valve 32 also maintains the pressure in the curler wrapping air bag 79 which is highly pressurized by the air pump 31 during measurement, and returns the pressure in the curler wrapping air bag 79 to the atmospheric pressure after the measurement is completed.

The pressure sensor 33 is means for detecting the pressure in the curler wrapping air bag 79, detects the pressure in the curler wrapping air bag 79 at the start of measurement, and outputs a signal corresponding to the detected value to an amplifier 38.

The amplifier 38 amplifies the signal output from the pressure sensor 33 and outputs the signal to an A/D converter 39. The A/D converter 39 digitizes the analog signal output from the amplifier 38 and outputs the signal to the CPU 40.

In this example, an output unit 42 includes the display 11 described above, and a printer 12.

In this example, an operation unit 43 includes the measurement start/stop switches 13A and 13B and the print instruction switch 14 described above.

The CPU 40 controls the measuring air system 20 and the curler wrapping air system 30 based on the command input to the operation unit 43, and outputs the measurement result to the output unit 42 and a memory unit 41. The memory unit 41 is means for storing the measurement result. Further, when the print instruction switch 14 is pressed, the CPU 40 causes the printer 12 to print out the measurement result on paper (roll paper in this example).

(Blood Pressure Measurement Operation)

FIG. 16 shows an operation flow of blood pressure measurement by the CPU 40 in the sphygmomanometer 1 configured as described above. In this example, when the subject presses the measurement start/stop switch 13A or 13B provided on the operation unit 43 of the main body 2 in the state of passing the upper arm 90 through the cuff unit 5, the operation is shifted to the measurement operation.

First, in step S1, the sphygmomanometer 1 is initialized. At this time, in the cuff unit 5 (cuff structure 7), as shown in FIG. 14A, the pressures in the measuring air bag 77 and the curler wrapping air bag 79 are both zero (atmospheric pressure). In this state (natural state), end parts of the curler 78 in the circumferential direction overlap with each other, and end parts of the measuring air bag 77 in the circumferential direction are relatively separated from each other.

Figure 14B:
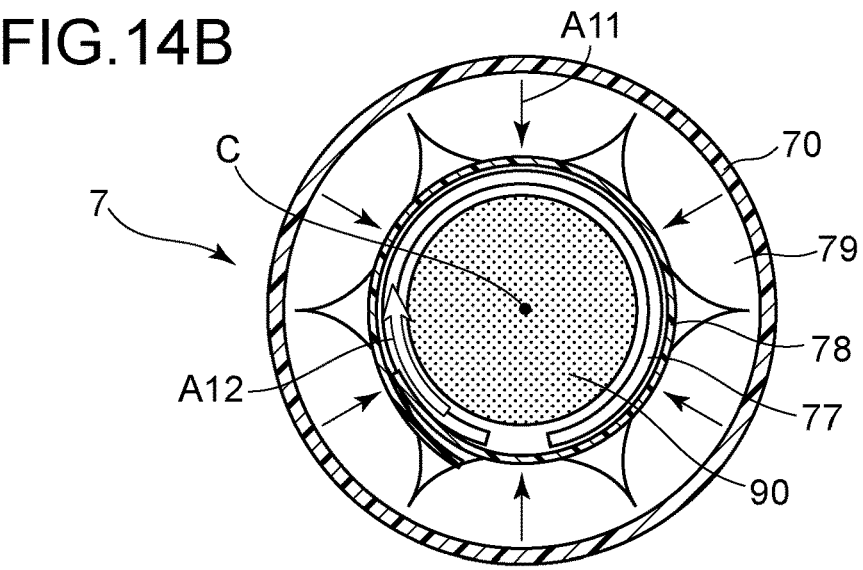
Figure 14C:
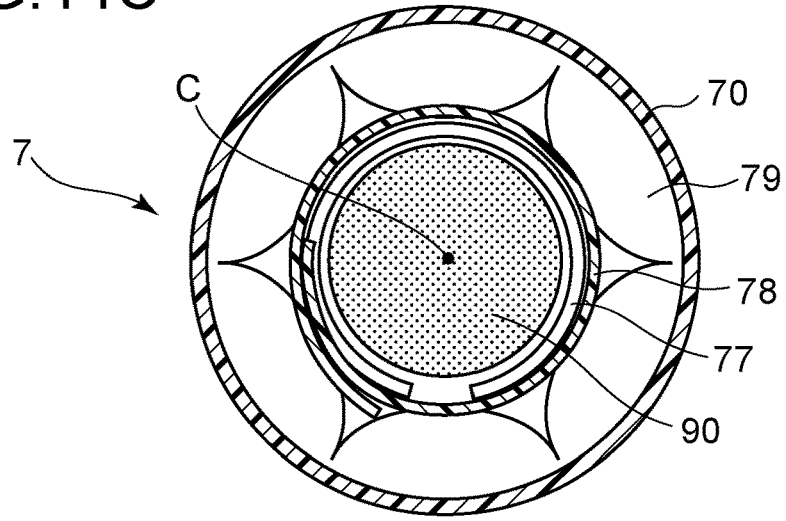

Next, in step S2 of FIG. 16, the CPU 40 acts as the pressure control unit and supplies the air from the air pump 31 to the curler wrapping air bag 79 via the fluid connectors 52, 53, 82, and 83. As a result, the curler wrapping air bag 79 is pressurized. At this time, in the cuff unit 5 (cuff structure 7), as shown by an arrow A11 in FIG. 14B, the curler wrapping air bag 79 expands inward in the radial direction to compress the curler 78 inward in the radial direction. As a result, an overlapped dimension of the end parts of the curler 78 in the circumferential direction increases as indicated by an arrow A12, and the end parts of the measuring air bag 77 in the circumferential direction approach each other. Then, when the pressure inside the curler wrapping air bag 79 reaches a predetermined pressure, the pressurization of the curler wrapping air bag 79 is completed (step S3). As a result, as shown in FIG. 14C, the upper arm 90 is surrounded by the measuring air bag 77.

Next, in step S4 of FIG. 16, the CPU 40 acts as the pressure control unit and supplies the air from the air pump 21 to the measuring air bag 77 via the fluid connectors 51 and 81. As a result, the measuring air bag 77 is pressurized. Then, when the pressure inside the measuring air bag 77 reaches a predetermined pressure, the pressurization of the measuring air bag 77 is completed, and in step S5, the depressurization of the measuring air bag 77 is started.

After that, in step S6, the CPU 40 functions as the blood pressure calculation unit, detects the arterial pressure pulse wave (pressure fluctuation component) based on the output of the pressure sensor 23, and calculates the blood pressure based on the detection data of the arterial pressure pulse wave (oscillometric method). When the calculation of the blood pressure value is completed, in step S7, the blood pressure value is displayed on the display 11 provided in the output unit 42 of the main body 2, and in step S8, the inside of the curler wrapping air bag 79 and the inside of the measuring air bag 77 are opened to the atmosphere.

Thus, according to the sphygmomanometer 1, the blood pressure can be easily measured by the subject. The blood pressure may be calculated in the pressurizing process instead of the depressurizing process.

(Component Replacement)

As a result of many years of use, for example, when the fluid bag (measuring air bag 77 or curler wrapping air bag 79) deteriorates and defects such as air leakage occur, only the cuff structure 7 of the cuff unit is replaced as a component in this sphygmomanometer 1.

Specifically, first, as shown in FIG. 10A, the rear part of the h-shaped protrusion 46 is pushed in the direction indicated by the arrow A0 (radially outward), and in the state of the axial locking of the lock part L being released, as shown in FIG. 10B, the cuff unit 5 is slid with respect to the slide receiving part 4 in the direction indicated by the arrow A2 (opposite to the attaching direction). At this time, the upper edges 4a1 and 4a2 on both sides of the front surface side portion 4a of the slide receiving part 4 abut with the lower edges 6a1 and 6a2 on both sides of the rear surface side portion 6a of the cover 6 to support the weight of the cuff unit 5. Therefore, the service person, etc. does not need to support the weight of the cuff unit 5 with one's own hand when sliding the cuff unit 5, and can slide the cuff unit 5 easily. After that, as shown by the arrow A6 in FIG. 11, the cuff unit 5 is lifted and detached from the main body 2 (slide receiving part 4).

Next, as shown in FIG. 6, the rear part of the L-shaped protrusion 71 is pushed in the direction indicated by the arrow A3 (radially inward), and in the state of the axial locking by the first engagement part E1 being released, the cover 6 is slid in the direction indicated by the arrow A4. Along with this, the restriction in relative movement by the second engagement part E2 in the radial direction R and the circumferential direction θ is also released. As a result, the cover 6 is detached from the cuff structure 7. After the detachment, the defective cuff structure 7 is discarded, for example.

Meanwhile, a new cuff structure 7 is prepared. The cover 6 (original cover 6) is detachably attached integrally to the new cuff structure 7 in the direction indicated by the arrow A5 in FIG. 6, to thereby constitute a new cuff unit 5.

Next, the new cuff unit 5 is slid and attached along the central axis C of the slide receiving part 4 in the reverse order of detachment. Specifically, the new cuff unit 5 is placed on the slide receiving part 4 in the direction indicated by the arrow A7 in FIG. 11. Next, the new cuff unit 5 is slid with respect to the slide receiving part 4 in the direction indicated by the arrow A1 in FIG. 10B. At this time, the upper edges 4a1 and 4a2 on both sides of the front surface side portion 4a of the slide receiving part 4 abut with the lower edges 6a1 and 6a2 on both sides of the rear surface side portion 6a of the cover 6 to support the weight of the cuff unit 5. Therefore, the service person, etc. who sets up this sphygmomanometer 1 does not need to support the weight of the cuff unit 5 with one's own hand when sliding the cuff unit 5, and can easily attach the cuff unit 5 by only pushing (sliding) the cuff unit 5 toward the slide end A1f side.

As described above, in this sphygmomanometer 1, only the cuff structure 7 of the cuff unit 5 is easily replaced as a component. In the set-up state, the new cuff structure 7 is covered by the cover 6 (original cover 6) and the slide receiving part 4.

Note that the cover 6 (original cover 6) of the cuff unit 5 is reused. If the main body 2 is discolored as a result of many years of use, the cover 6 (original cover 6) should be discolored as well. Therefore, there is no difference in color between the main body 2 and the cover 6 (original cover 6). Therefore, according to this sphygmomanometer 1, even if the component (cuff structure 7) is replaced, the replacement does not give the user odd feeling.

(Modification)

Figure 13:
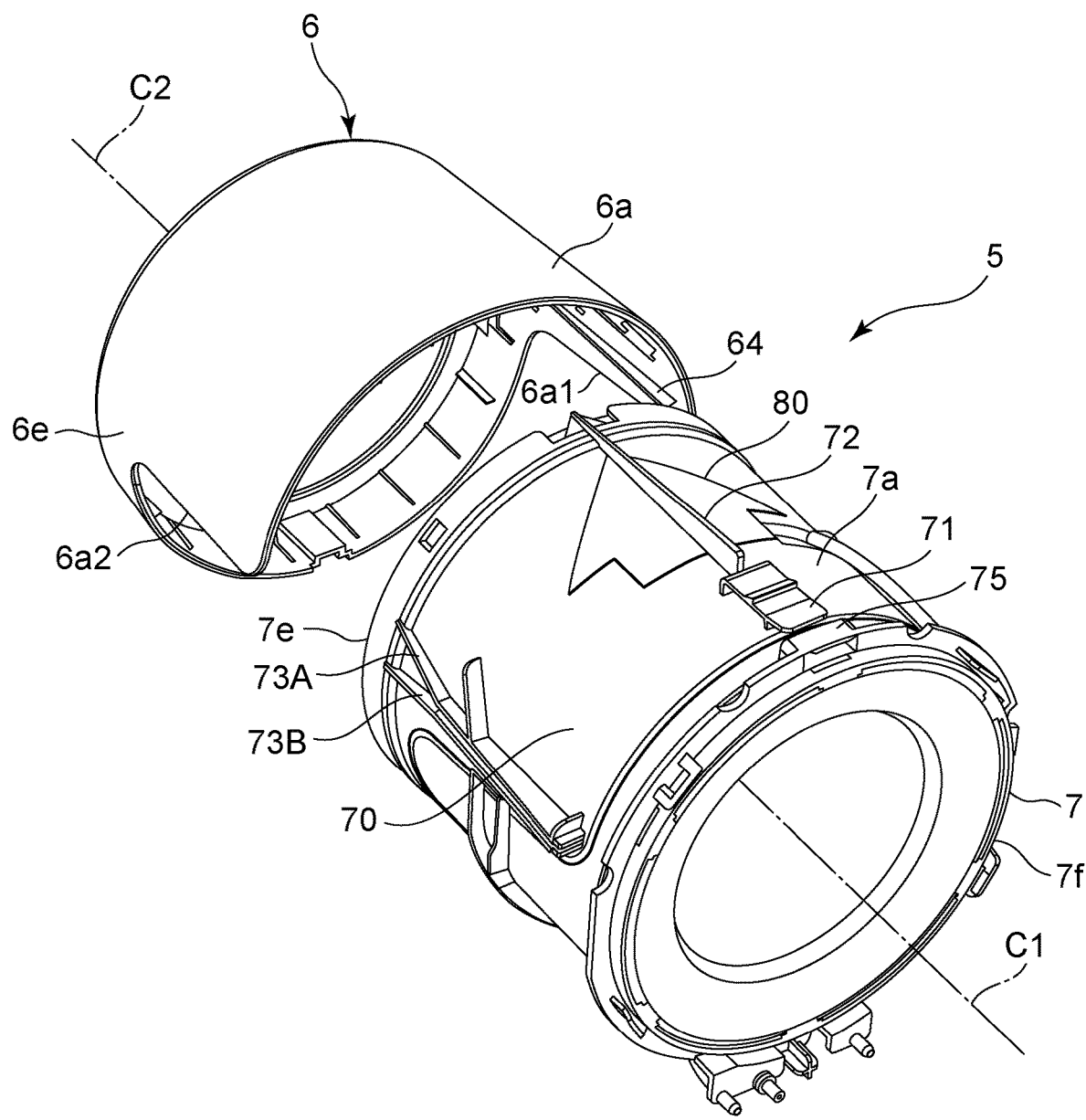
FIG. 13 is a diagram showing a mark provided on an upper part of an outer circumferential surface of the cuff structure, the mark indicating an orientation when the cover is attached.

As shown in FIG. 13, a mark 80 indicating the relative sliding direction when the cover 6 is attached to the cuff structure 7 may be provided on the outer circumferential surface 7a of the cuff structure 7 constituting the cuff unit 5. In this example, the mark 80 is in the form of a thick arrow extending from the rear surface 7f side to the front surface 7e side of the cuff structure 7. The service person, etc. can relatively slide the cover 6 in the correct direction along the upper half of the outer circumferential surface 7a of the cuff structure 7 by looking at the mark 80 when attaching the cover 6 to the cuff structure 7. That is, in this example, the service person, etc. is urged to slip and slide the outer circumferential surface 7a of the cuff structure 7 from the front surface 7e side of the cuff structure 7 against the cover 6. Therefore, the service person, etc. can correctly and more easily attach the cover 6 to the cuff structure 7. The mark 80 indicating the relative slide direction may be provided not only on the cuff structure 7 but also on one or both of the cuff structure 7 and the cover 6.

In this embodiment, the measurement target site inserted into the cuff unit 5 is the upper arm 90; however, the measurement target site is not limited to this. The measurement target site may be a wrist, a finger, a lower limb, or others.

Further, in this embodiment, the cuff unit 5 is configured such that the base member 70 includes the curler wrapping air bag 79, the curler 78, and the measuring air bag 77; however, the present invention is not limited to this. The curler wrapping air bag 79 and the curler 78 may be omitted, and only the measuring air bag 77 may compress the measurement target site.

As described above, a sphygmomanometer of the present disclosure comprises:
a main body accommodating a pump; and
a cuff unit having a cylindrical shape and detachably attached to the main body,
wherein the main body includes a slide receiving part having a circular-arc cross section that opens upward and slidably receiving the cuff unit along a direction perpendicular to the circular-arc cross section,
wherein the slide receiving part is tilted horizontally or in a manner of gradually increasing in height toward a slide end side in a sliding direction of sliding the cuff unit,
wherein the cuff unit includes
a cuff structure having a cylindrical shape so as to allow a measurement target site having a rod shape to be inserted, and having a fluid bag along an inner circumferential surface, and
a cover having a circular-arc cross section that opens downward, and detachably attached integrally to the cuff structure to cover at least an upper half of the cuff structure, and
wherein, when the cuff unit is slid along the slide receiving part, upper edges of both sides of the circular-arc cross section of the slide receiving part come into contact with lower edges of both sides of the circular-arc cross section of the cover to support a weight of the cuff unit.

Here, with respect to the cuff unit, "down" in the "downward" and "upper" in the "upper half" refer to the sides that become "lower" and "upper" sides, respectively, in a state of the cuff unit being attached to the main body.

In the sphygmomanometer of the present disclosure, in order to set up a state in which blood pressure can be measured, first, a cover is detachably attached to the cuff structure integrally to constitute the cuff unit. Next, the cuff unit is slid and attached along the slide receiving part (having a circular-arc cross section). At this time, upper edges on both sides of a circular-arc cross section of the slide receiving part come into contact with lower edges on both sides of a circular-arc cross section of the cover to support the weight of the cuff unit. Therefore, for example, a service person, a person in charge of equipment, a user, or the others who set up this sphygmomanometer (hereinafter referred to as "service person, etc.") does not need to support the weight of the cuff unit by oneself when sliding the cuff unit, and can easily attach the cuff unit by only pushing (sliding) the cuff unit toward the slide end side. In particular, when the slide receiving part is tilted in a manner that its height gradually decreases toward the slide end side, the service person, etc. can use the gravity to the cuff unit, and can therefore attach the cuff unit more easily.

During blood pressure measurement, in a state of the subject inserting a rod-shape measurement target site (upper arm, wrist, finger, lower limb, etc.) into the cuff unit, a fluid is supplied from the pump of the main body to the fluid bag of the cuff unit to compress the measurement target site. Thereby, the blood pressure measurement is performed. The "fluid" is typically air, but may be other gas or liquid.

When, for example, the fluid bag becomes deteriorated as a result of many years of use and defects such as air leakage occurs, only the cuff structure of the cuff unit is replaced as a component in the sphygmomanometer of the present disclosure. That is, first, the cuff unit is slid and detached from the slide receiving part in a direction opposite to the attaching direction (the direction toward the slide end side). At this time, upper edges on both sides of a circular-arc cross section of the slide receiving part come into contact with lower edges on both sides of a circular-arc cross section of the cover to support the weight of the cuff unit. Therefore, the service person does not need to support the weight of the cuff unit with one's own hand when sliding the cuff unit, and can easily detach the cuff unit. Next, the cover of the cuff unit is detached from the cuff structure (After the detachment, the defective cuff structure is discarded, for example). On the other hand, a new cuff structure is prepared. The above-mentioned cover (original cover) is detachably attached to the new cuff structure integrally to constitute a new cuff unit. Next, the new cuff unit is slid and attached along the slide receiving part in the reverse order of detachment. At this time, upper edges on both sides of a circular-arc cross section of the slide receiving part come into contact with lower edges on both sides of a circular-arc cross section of the cover to support the weight of the cuff unit. Therefore, for example, the service person, etc. who sets up this sphygmomanometer does not need to support the weight of the cuff unit with one's own hand when sliding the cuff unit, and can easily attach the cuff unit by only pushing (sliding) the cuff unit toward the slide end side. As described above, in the sphygmomanometer of the present disclosure, only the cuff structure of the cuff unit is easily replaced as a component. In the set-up state, the new cuff structure is covered by the cover (original cover) and the slide receiving part.

Note that the cover (original cover) of the cuff unit is reused. If the main body is discolored as a result of many years of use, the cover (original cover) should be discolored as well. Therefore, there is no difference in color between the main body and the cover (original cover). Therefore, according to this sphygmomanometer, even if the component (cuff structure) is replaced, the replacement does not give the user odd feeling.

In the sphygmomanometer of the one embodiment, the slide receiving part has a first fluid connector communicating with the pump at a portion corresponding to the slide end side, wherein the cuff unit has a second fluid connector communicating with the fluid bag at a portion facing the first fluid connector, and wherein, when the cuff unit is slidably attached along the slide receiving part toward the slide end side, the first fluid connector and the second fluid connector are connected to each other by fitting in fluid flowable and detachably attached manners.

In the sphygmomanometer of the one embodiment, when the cuff unit is slidably attached toward the slide end side along the slide receiving part, the first fluid connector and the second fluid connector are connected with each other by fitting in fluid flowable and detachably attached manners. During blood pressure measurement, in the state of the subject inserting the measurement target site into the cuff unit, the fluid is supplied from the pump of the main body to the fluid bag of the cuff unit through the first and second fluid connectors to cause the measurement target site to be compressed. Thereby, the blood pressure measurement is performed. Here, in the attached state in which the cylindrical cuff unit is received in the slide receiving part having the circular-arc cross section that opens upward, external force in a direction perpendicular to the sliding direction is hardly applied between the slide receiving part and the cuff unit, which causes twisting hardly occurs. Therefore, the reliability of the fluid flowable connection between the first and second fluid connectors is enhanced. Conversely, when the cuff unit is slid and detached from the slide receiving part in the direction opposite to the attaching direction, the connection between the first and second fluid connectors is released. Thus, the first fluid connector and the second fluid connector are attached or detached by attaching or detaching the cuff unit to or from the slide receiving part. Therefore, the service person, etc. can easily set up and/or disassemble this sphygmomanometer.

In the sphygmomanometer of the one embodiment, the cuff unit includes, in order to detachably attach the cover to the cuff structure integrally, and by the cover being slid along the upper half of the outer circumferential surface of the cuff structure from a front surface side arranged facing a subject during blood pressure measurement toward a rear surface side opposite to the front surface side:

a first engagement part that detachably engages and locks the cuff structure with the cover in an axial direction of the cuff structure; and a second engagement part that restricts relative movement between the cuff structure and the cover in a radial direction and a circumferential direction of the cuff structure.

The "axial direction" of the cuff structure indicates a direction along the central axis of the cuff structure. The "radial direction" of the cuff structure indicates a direction perpendicular to the central axis of the cuff structure. The "circumferential direction" of the cuff structure indicates a direction around the central axis of the cuff structure.

In the sphygmomanometer of the one embodiment, along the upper half of the outer circumferential surface of the cuff structure, by the cover being slid from the front surface side facing the subject during blood pressure measurement toward the rear surface side opposite to the front surface side, the first engagement part detachably engages and locks the cuff structure with the cover in the axial direction of the cuff structure. At the same time, the second engagement part restricts the relative movement between the cuff structure and the cover in the radial direction and the circumferential direction of the cuff structure. As a result, the service person, etc. can detachably attach the cover to the cuff structure integrally even with a simple operation of sliding the cover along the upper half of the outer circumferential surface of the cuff structure, such that the cuff unit is integrally constituted. Conversely, when the cover is detached from the cuff structure, the axial locking by the first engagement part is released, and the cover is slid from the rear surface side toward the front surface side along the central axis in the upper half of the outer circumferential surface of the cuff structure. This allows the cover to be detached from the cuff structure.

In the sphygmomanometer of the one embodiment, the first engagement part is configured to generate a sound indicating completion of locking.

In the sphygmomanometer of the one embodiment, the service person, etc. can know that the cover is correctly attached to the cuff structure by listening to the sound indicating the completion of the locking by the first engagement part. As a result, the service person, etc. can surely proceed with the setup of this sphygmomanometer.

In the sphygmomanometer of the one embodiment, one or both of the cuff structure and the cover are provided with a mark indicating a relative sliding direction when the cover is attached to the cuff structure.

In the sphygmomanometer of the one embodiment, the service person, etc. looks at the mark when attaching the cover to the cuff structure, accordingly, can relatively slide the cover in a correct orientation along the upper half of the outer circumferential surface of the cuff structure. Therefore, a service person, etc. can correctly and more easily attach the cover to the cuff structure.

In the sphygmomanometer of the one embodiment, the sphygmomanometer comprises a lock part that detachably engages and locks the main body with the cuff unit in the sliding direction by the cuff unit being slid toward the slide end side along the slide receiving part.

In the sphygmomanometer of the one embodiment, the cuff unit is slid toward the slide end side along the slide receiving part, accordingly, the lock part detachably engages and locks the main body and the cuff unit in the sliding direction. Thereby, a service person, etc. can detachably lock the main body and the cuff unit with each other in the sliding direction with the simple operation of pushing (sliding) the cuff unit toward the slide end side along the slide receiving part. As a result, this sphygmomanometer can be integrally constituted.

In the sphygmomanometer of the one embodiment, the lock unit is configured to generate a sound indicating completion of locking.

In the sphygmomanometer of the one embodiment, a service person, etc. can know that the cuff unit is correctly attached to the main body by listening to the sound indicating the completion of the locking by the lock part. As a result, the service person, etc. can surely proceed with the setup of this sphygmomanometer.

In the sphygmomanometer of the one embodiment, the cover has an annular shape at an end face on a front surface side arranged facing the subject during blood pressure measurement, so as to cover an end face on the front side of the cuff structure.

In the sphygmomanometer of the one embodiment, in the set-up state, the cuff structure is covered by the cover and the slide receiving part, and in particular, the end surface on the front surface side of the cuff structure is covered by the end surface on the front surface side of the cover. Therefore, even if the cuff structure is replaced due to defects, for example, the user cannot recognize that the cuff structure has been replaced from the appearance in the set-up state. Therefore, the user is prevented from feeling odd.

In the sphygmomanometer of the one embodiment, the main body includes, with the cuff unit attached to the body,
a pressure control unit that supplies a fluid from the pump to the fluid bag and performs control to compress the measurement target site inserted into the cuff unit, and
a blood pressure calculation unit that calculates blood pressure based on a pressure of the fluid.

In the sphygmomanometer of the one embodiment, during blood pressure measurement, the pressure control unit performs control to supply the fluid from the pump mounted on the main body to the fluid bag and to compress the measurement target site inserted into the cuff unit. In the process of pressurizing or depressurizing the cuff structure (including the fluid bag), the blood pressure calculation unit calculates the blood pressure based on the pressure of the fluid (using the oscillometric method). Therefore, the blood pressure can be easily measured by the subject.

The above embodiments are illustrative, and various modifications can be made without departing from the scope of the present invention. It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. A sphygmomanometer comprising:
a main body accommodating a pump; and
a cuff unit having a cylindrical shape and detachably attached to the main body,
wherein the main body includes a slide receiving part having a circular-arc cross section that opens upward and slidably receiving the cuff unit along a direction perpendicular to the circular-arc cross section, the slide receiving part including upper edges at both ends of the circular-arc cross section,
wherein the slide receiving part is tilted horizontally or in a manner of gradually increasing in height toward a slide end side in a sliding direction of sliding the cuff unit,
wherein the cuff unit includes
a cuff structure having a cylindrical shape extending over an entire circumference of the cuff structure so as to allow a measurement target site having a rod shape to be inserted, and having a fluid bag along an inner circumferential surface, and
a cover having a circular-arc cross section that opens downward, and detachably attached integrally to the cuff structure to cover at least an upper half of the cuff structure, and
wherein, when the cuff unit is slid along the slide receiving part, the upper edges of both sides of the circular-arc cross section of the slide receiving part come into contact with lower edges of both sides of the circular-arc cross section of the cover to support a weight of the cuff unit.

2. The sphygmomanometer according to claim 1,
wherein the slide receiving part has a first fluid connector communicating with the pump at a portion corresponding to the slide end side,
wherein the cuff unit has a second fluid connector communicating with the fluid bag at a portion facing the first fluid connector, and
wherein, when the cuff unit is slidably attached along the slide receiving part toward the slide end side, the first fluid connector and the second fluid connector are connected to each other by fitting in fluid flowable and detachably attached manners.

3. The sphygmomanometer according to claim 1,
wherein the cuff unit includes,
in order to detachably attach the cover to the cuff structure integrally,
a first engagement part having a hook arranged on the cuff structure, and a slot arranged on the cover, and
a second engagement part having a rib arranged on the one of the cuff structure and the cover, and a guide rib arranged on the other of the cuff structure and the cover, wherein
by the cover being slid along the upper half of the outer circumferential surface of the cuff structure from a front surface side arranged facing a subject during blood pressure measurement toward a rear surface side opposite to the front surface side:
the first engagement part detachably engages and locks the cuff structure with the cover in an axial direction of the cuff structure; and
the second engagement part restricts relative movement between the cuff structure and the cover in a radial direction and a circumferential direction of the cuff structure.

4. The sphygmomanometer according to claim 3,
wherein the first engagement part is configured to generate a sound indicating completion of locking.

5. The sphygmomanometer according to claim 3,
wherein one or both of the cuff structure and the cover are provided with a mark indicating a relative sliding direction when the cover is attached to the cuff structure.

6. The sphygmomanometer according to claim 1,
further comprising a lock part that detachably engages and locks the main body with the cuff unit in the sliding direction by the cuff unit being slid toward the slide end side along the slide receiving part.

7. The sphygmomanometer according to claim 6,
wherein the lock part is configured to generate a sound indicating completion of locking.

8. The sphygmomanometer according to claim 1,
wherein the cover has an annular shape at an end face of the cover on a front surface side of the cover arranged facing a subject during blood pressure measurement, so as to cover an end face of the cuff structure on a front surface side of the cuff structure.

9. The sphygmomanometer according to claim 1,
wherein the main body includes a processor programmed to:
act as a pressure control unit configured to supply, when the measurement target site is inserted into the cuff unit in a state of the cuff unit being attached to the main body, a fluid from the pump to the fluid bag to compress the measurement target site, and
act as a blood pressure calculation unit configured to calculate blood pressure based on a pressure of the fluid.

* * * * *